(12) United States Patent
Macrae et al.

(10) Patent No.: US 9,993,516 B2
(45) Date of Patent: Jun. 12, 2018

(54) TREATMENT OF LEFT VENTRICULAR NON-COMPACTION AND DILATED CARDIOMYOPATHY BY INHIBITING MELANOCORTIN RECEPTOR FOUR

(71) Applicant: THE BRIGHAM AND WOMEN'S HOSPITAL, INC., Boston, MA (US)

(72) Inventors: Calum Macrae, Wellesley Hills, MA (US); Anne-Karin Kahlert, Dresden (DE)

(73) Assignee: THE BRIGHAM AND WOMEN'S HOSPITAL, INC., Boston, MA (US)

(*) Notice: Subject to any disclaimer, the term of this patent is extended or adjusted under 35 U.S.C. 154(b) by 0 days. days.

(21) Appl. No.: 15/037,693

(22) PCT Filed: Nov. 19, 2014

(86) PCT No.: PCT/US2014/066406
§ 371 (c)(1),
(2) Date: May 19, 2016

(87) PCT Pub. No.: WO2015/077334
PCT Pub. Date: May 28, 2015

(65) Prior Publication Data
US 2016/0296587 A1 Oct. 13, 2016

Related U.S. Application Data

(60) Provisional application No. 61/906,066, filed on Nov. 19, 2013.

(51) Int. Cl.
A61P 9/04 (2006.01)
A61K 38/06 (2006.01)
A61K 38/10 (2006.01)
A61K 38/12 (2006.01)
A61K 38/17 (2006.01)
A61K 31/00 (2006.01)
A61K 38/08 (2006.01)
A61N 1/39 (2006.01)
A61N 1/362 (2006.01)

(52) U.S. Cl.
CPC .............. *A61K 38/06* (2013.01); *A61K 31/00* (2013.01); *A61K 38/08* (2013.01); *A61K 38/10* (2013.01); *A61K 38/12* (2013.01); *A61K 38/17* (2013.01); *A61N 1/362* (2013.01); *A61N 1/39* (2013.01)

(58) Field of Classification Search
None
See application file for complete search history.

(56) References Cited

U.S. PATENT DOCUMENTS

2010/0129319 A1  5/2010  Lindquist et al.
2010/0173845 A1  7/2010  Bevec

OTHER PUBLICATIONS

Sebhat et al, 2003. Chapter 4 in Annual Reports in Medicinal Chemistry. 38: 31-40.*
Pontillo et al, 2005. Biological & Medicinal Chemistry Letters. 2541-2546.*
Chen et al 2008. Bioorganic & Medicinal Chemistry Letter. 18: 129-136.*
Tran et al 2007. Bioorganic & Medicinal Chemistry. 15: 5166-5176.*
Xi et al. 2003. Bioorganic & Medicinal Letter. 14: 377-381.*
Chaki et al, 2005. Pharm Biochem Behav. 82: 621-626.*
Dallman et al, 2011. J Cachexia Sarcopenia Muscle. 2: 163-174.*
Arndt et al., "Fine Mapping of the 1p36 Deletion Syndrome Identifies Mutation of PRDM16 as a Cause of Cardiomyopathy", The American Journal of Human Genetics 93(1):67-77 (2013).
Herman et al., "Truncations of Titin Causing Dilated Cardiomyopathy", N Engl J Med. 366(7):619-628 (2012).

* cited by examiner

Primary Examiner — Zachary Howard
(74) Attorney, Agent, or Firm — Nixon Peabody LLP; David S. Resnick

(57) ABSTRACT

The present disclosure provides methods and compositions for treatment of left ventricular non-compaction and dilated cardiomyopathies.

13 Claims, 26 Drawing Sheets

TREATMENT OF LEFT VENTRICULAR NON-COMPACTION AND DILATED CARDIOMYOPATHY BY INHIBITING MELANOCORTIN RECEPTOR FOUR

CROSS REFERENCE TO RELATED APPLICATIONS

This application is a 371 National Phase Entry of International Patent Application No. PCT/US2014/066406 filed on Nov. 19, 2014 which claims benefit under 35 U.S.C. § 119(e) of U.S. Provisional Patent Application Ser. No. 61/906,066 filed Nov. 19, 2013, the contents of which are incorporated herein by reference in their entirety.

SEQUENCE LISTING

The sequence listing of the present application has been submitted electronically via EFS-Web as an ASCII formatted sequence listing with a file name "043214-079621-PCT_SL", creation date of May 17, 2016 and a size of 3,023 bytes. The sequence listing submitted via EFS-Web is part of the specification and is herein incorporated by reference in its entirety.

TECHNICAL FIELD

The present disclosure relates generally uses of MC4R antagonists to treat left ventricular non-compaction and dilated cardiomyopathy.

BACKGROUND

Left Ventricular Non-Compaction

Non-compaction cardiomyopathy (NCC), also called spongiform cardiomyopathy, is a rare congenital cardiomyopathy that affects both children and adults. (Pignatelli R H, McMahon C J, Dreyer W J, et al (November 2003). "Clinical characterization of left ventricular noncompaction in children: a relatively common form of cardiomyopathy." Circulation 108 (21): 2672-8.) It results from the failure of myocardial development during embryogenesis. (Espinola-Zavaleta, Nilda; Soto, Elena; Castellanos, Luis Munoz; Játiva-Chávez, Silvio; Keirns, Candace. (2006). "Non-compacted Cardiomyopathy: Clinical-Echocardiographic Study" Cardiovasc. Ultrasound 4 (1): 35).

During development, the majority of the heart muscle is a sponge-like meshwork of interwoven myocardial fibers. As normal development progresses, these trabeculated structures undergo significant compaction that transforms them from spongy to solid. This process is particularly apparent in the ventricles, and particularly so in the left ventricle. Noncompaction cardiomyopathy results when there is failure of this process of compaction. Because the consequence of non-compaction is particularly evident in the left ventricle, the condition is also called left ventricular noncompaction (LVNV). LVNC is a cardiomyopathy characterized anatomically by deep trabeculations in the ventricular wall, which define recesses communicating with the main ventricular chamber. Other hypotheses and models have been proposed, none of which is as widely accepted as the noncompaction model.

Current diagnostic criteria for left ventricular non-compaction (LVNC) are controversial and often poorly correlate with outcomes. (A Cardiac Magnetic Resonance Imaging (cMRI) Based Approach to Diagnosis and Quantification of LV Non-compaction Using Relative Signal Intensities Top of Form P. Choudhary, S. Grieve, C. Semsarian, D. Richmond, D. Celermajer, R. Puranik Heart, Lung and Circulation Volume 22, Supplement 1, Page S162, 2013).

Dilated Cardiomyopathy

There are several different types of cardiomyopathy. Dilated cardiomyopathy (DC) is the most common form. Dilated cardiomyopathy is a disease of the heart muscle, primarily affecting your heart's main pumping chamber (left ventricle). The left ventricle becomes enlarged (dilated) and can't pump blood to your body with as much force as a healthy heart can.

Dilated cardiomyopathy doesn't necessarily cause symptoms, but for some people the disease is life-threatening. Dilated cardiomyopathy is a common cause of heart failure, the inability of the heart to supply the body's tissue and organs with enough blood. Dilated cardiomyopathy may also cause irregular heartbeats (arrhythmia), blood clots or sudden death.

Dilated cardiomyopathy may affect people of all ages, including infants and children. Treatments may be available for the underlying cause of dilated cardiomyopathy, or to improve blood flow and reduce symptoms.

Most people who have heart failure need to take medicines. Some medicines treat symptoms. Others may help prevent your heart failure from becoming worse or may prevent other heart problems.

Current Treatment for Left Ventricular Non-Compaction and Dilated Cardiomyopathy So far only management programs similar to management programs for other types of cardiomyopathies are available which include the use of angiotensin-converting enzyme (ACE) inhibitors to improve your heart's pumping capability, such as enalapril (Vasotec), lisinopril (Zestril, Prinivil), ramipril (Altace) and captopril (Capoten); angiotensin receptor blockers (ARBs) for those who can't take ACE inhibitors, such as losartan (Cozaar) and valsartan (Diovan); beta blockers to improve heart function, such as carvedilol (Coreg) and metoprolol (Lopressor, Toprol-XL); digoxin (Lanoxin) also referred to as digitalis, increases the strength of your heart muscle contractions and also tends to slow the heartbeat. Digoxin reduces heart failure symptoms and improves your ability to live with cardiomyopathy; diuretics to increase urination and keep fluid from collecting in your body. Commonly prescribed diuretics for heart failure include bumetanide (Bumex) and furosemide (Lasix). The drugs also decrease fluid in your lungs, so you can breathe more easily. One diuretic, spironolactone (Aldactone), may also be helpful in treating scarring of your heart tissue.

Another option for some people with dilated cardiomyopathy is a special pacemaker that coordinates the contractions between the left and right ventricles (biventricular pacing). In people who may be at risk of serious arrhythmias, drug therapy or an implantable cardioverter-defibrillator (ICD) may be options. An ICD is a small device—about the size of a box of matches—implanted in your chest to continuously monitor your heart rhythm and deliver electrical shocks when needed to control abnormal, rapid heartbeats. The device can also work as a pacemaker. In severe cases, Heart bypass (CABG) surgery or angioplasty to improve blood flow to the damaged or weakened heart muscle or Valve replacement or repair might be necessary. Chronic heart failure becomes worse over time. Many people who have heart failure will die from the condition. Heart failure is most often a chronic illness, which may get worse over time. Some people develop severe heart failure, in which medicines, other treatments, and surgery no longer help. Many people are at risk for deadly heart rhythms, and may need medicines or a defibrillator.

A heart transplant may be recommended for patients who have failed all the standard treatments and still have very severe symptoms as well as placement of a left ventricular assist device or artificial heart. However, there remains a need in the art for compositions and methods for treatment of left ventricular non-compaction and dilated cardiomyopathies.

SUMMARY OF THE INVENTION

The various aspects disclosed herein are based, in part, on inventors' discovery that melanocortin receptor (MCR) antagonists, such as melanocortin receptor four (MC4R) antagonists, can rescue cardiomyopathy.

In one aspect, the disclosure provides novel therapy for treating left ventricular non-compaction or dilated cardiomyopathy. Generally, the method comprises administering a therapeutically effective amount of a MCR antagonist to a subject in need thereof.

The inventors has also discovered that MCR antagonists, such as MC4R antagonist can also rescue heart failure in a zebrafish model of arrhythmogenic right ventricular cardiomyopathy (ARVC) can also be rescued with MCR4 antagonists. Accordingly, the disclosure also provides a method for treating ARVC comprising administering a therapeutically effective amount of a MCR antagonist to a subject in need for treatment of ARVC.

In some embodiments, the MCR antagonist is a MC4R antagonist. In some embodiments, the MCR antagonist is selected from the group consisting of:

(MCL0020, SEQ ID NO: 1)
Ac-D-2-Nal-Arg-2-Nal-NH$_2$, (SHU9119, SEQ ID NO: 2)
Ac-Nle-cyclo(Asp-His-D-2-Nal-Arg-Trp-Lys)-NH$_2$, (HS014, SEQ ID NO: 3)
Ac-Cys-Glu-His-D-2-Nal-Arg-Trp-Gly-Cys-Prol-Pro-Lys-Asp-NH$_2$, (HS024, SEQ ID NO: 4)
Ac-Cys-Nle-Arg-His-D-Nal-Arg-Trp-Gly-Cys-NH$_2$, and any combinations thereof.

Other features and advantages of the invention will become apparent from the following detailed description, taken in conjunction with the accompanying drawings, which illustrate, by way of example, various features of embodiments of the invention.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 10A shows echocardiographs of adult PRDM16 mutant zebrafish (right panel) and their wildtype age-matched siblings (left panel). FIG. 10B is a bar graph showing a decreased aortic peak velocity in PRDM16 mutant zebrafish model compared to their wildtype siblings.

DETAILED DESCRIPTION OF THE INVENTION

Figure 1A:
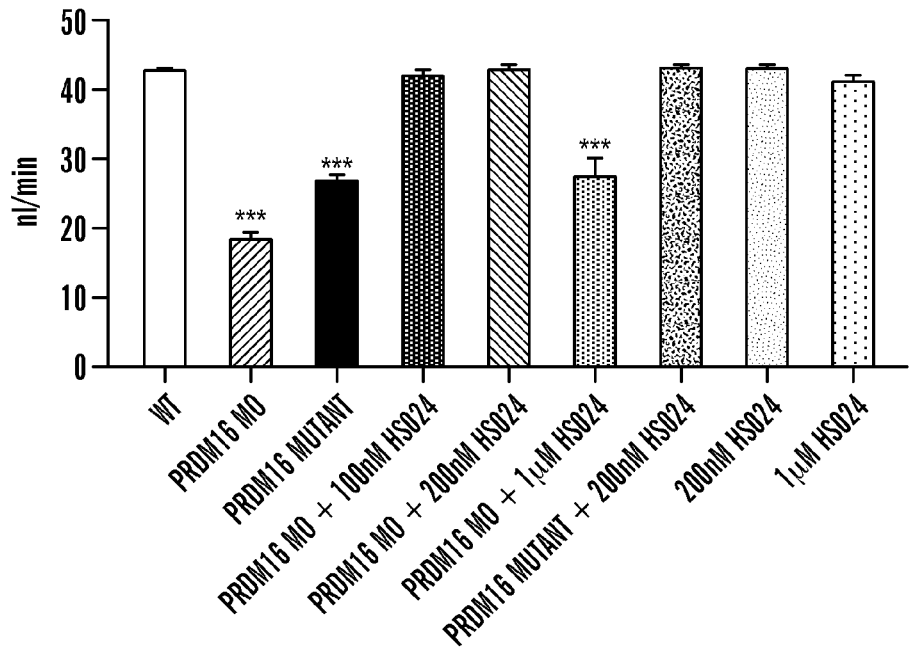
FIGS. 1A-1F are bar graphs showing reduced cardiac output can be rescued with MCR4 antagonists HS024 (FIG. 1A), HS014 (FIG. 1B), MC4R MO (morpholino against MC4 receptor)(FIG. 1C), JKC363 (FIG. 1D), MCL00200 (FIG. 1E), and SU9119 (FIG. 1F).
Figure 1B:
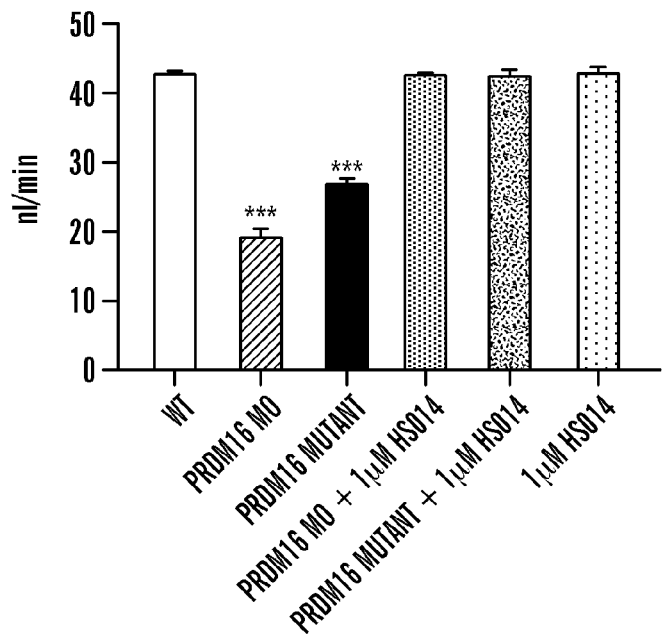
Figure 1C:
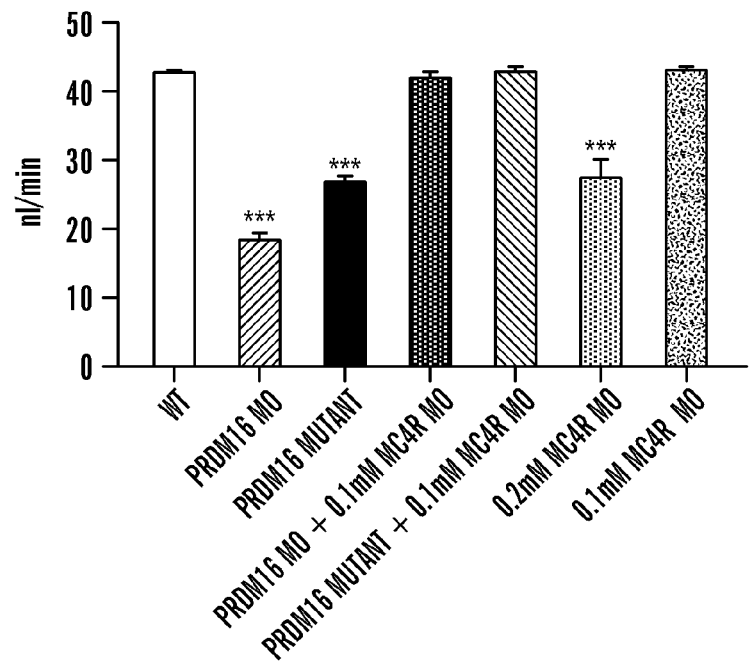
Figure 1D:
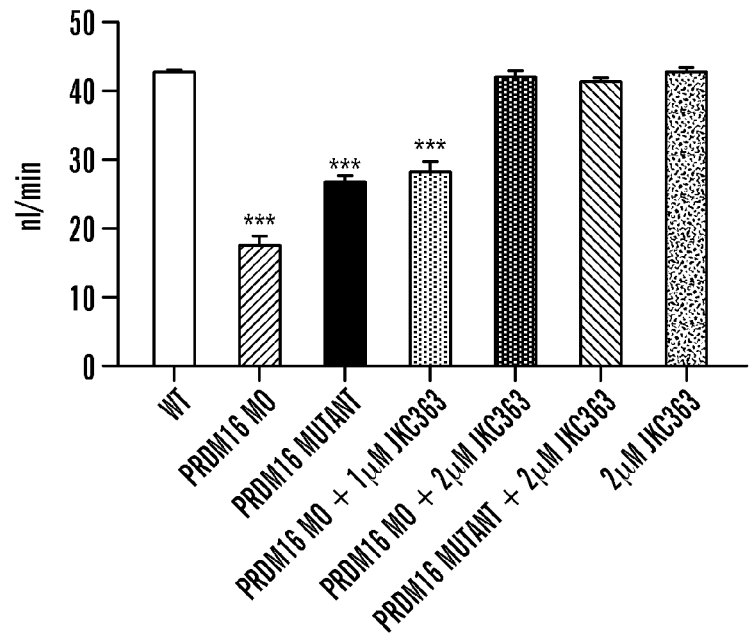
Figure 1E:
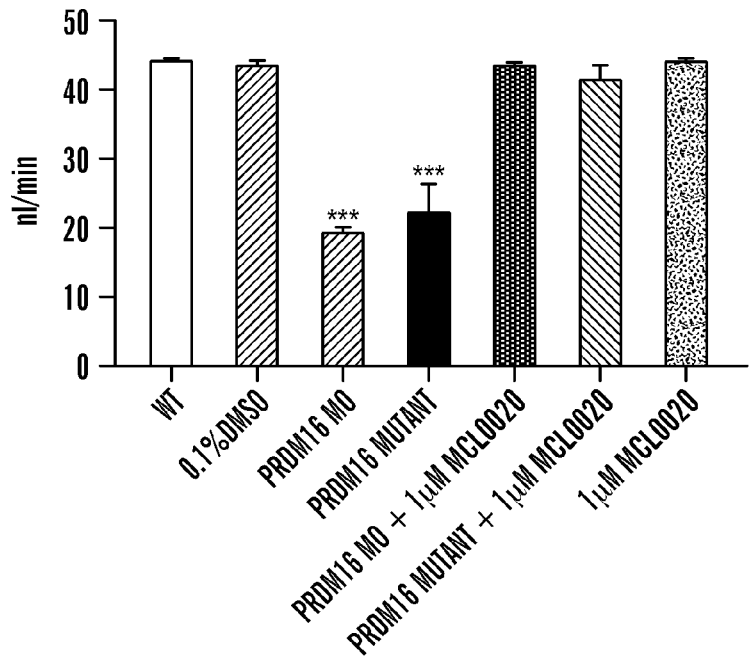
Figure 1F:
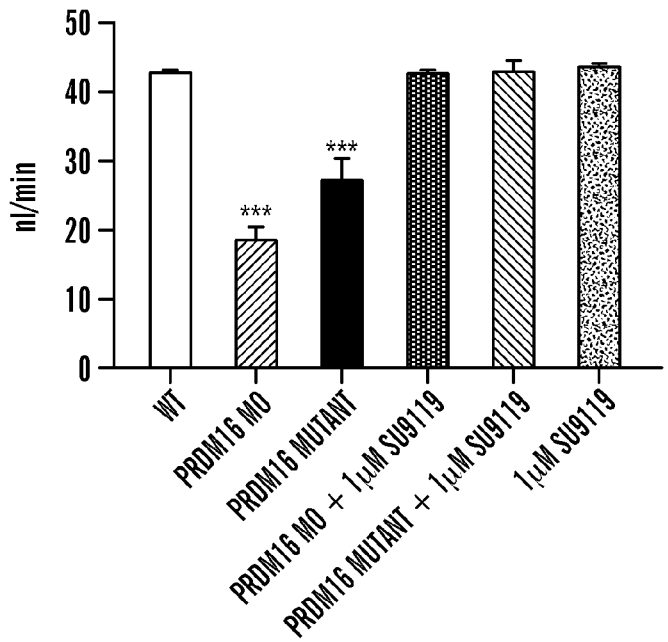
Figure 2:
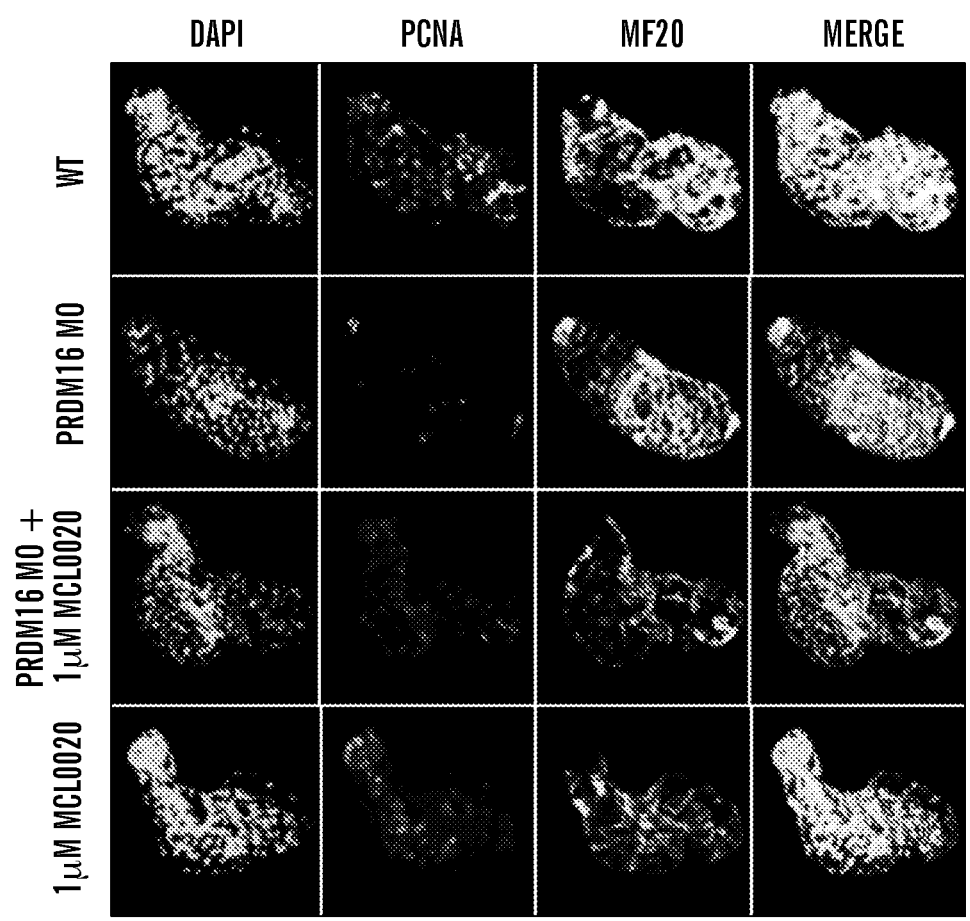
FIG. 2 shows 2 day old isolated zebrafish hearts, left panel indicates nuclear staining with DAPI, middle panel shows staining with proliferation marker PCNA, right panel shows staining with cardiomyocyte marker MF20.
Figure 3A:
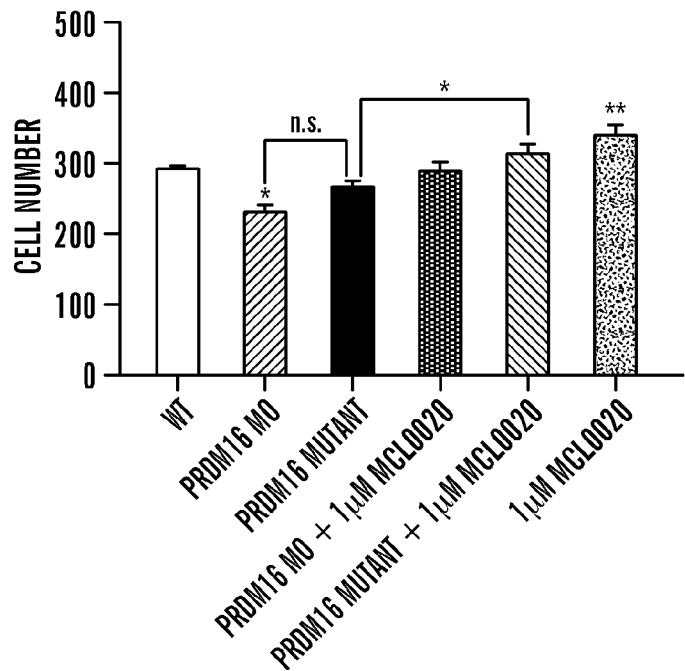
FIGS. 3A-3L are bar graph showing decreased proliferation can be prevented or reduced with MCR4 antagonists MCL0020 (FIGS. 3A and 3B), HS024 (FIGS. 3C and 3D), SU9119 (FIGS. 3E and 3F), MO (FIGS. 3G and 3H), HS014 (FIGS. 3I and 3J), and JKC363 (FIGS. 3K and 3L).
Figure 3B:
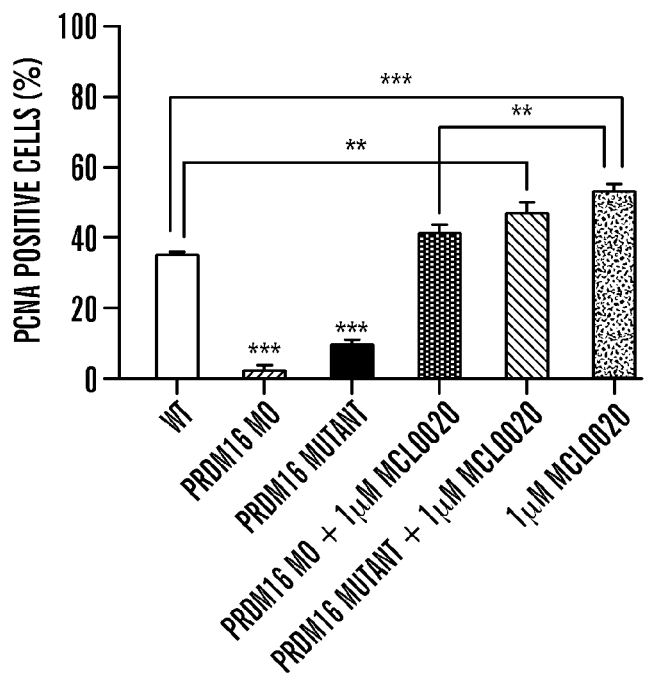
Figure 3C:
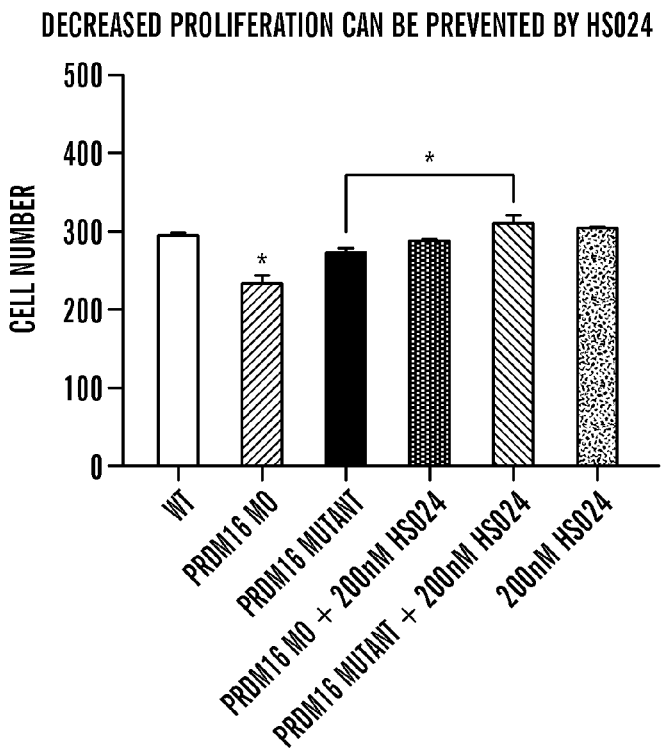
Figure 3D:
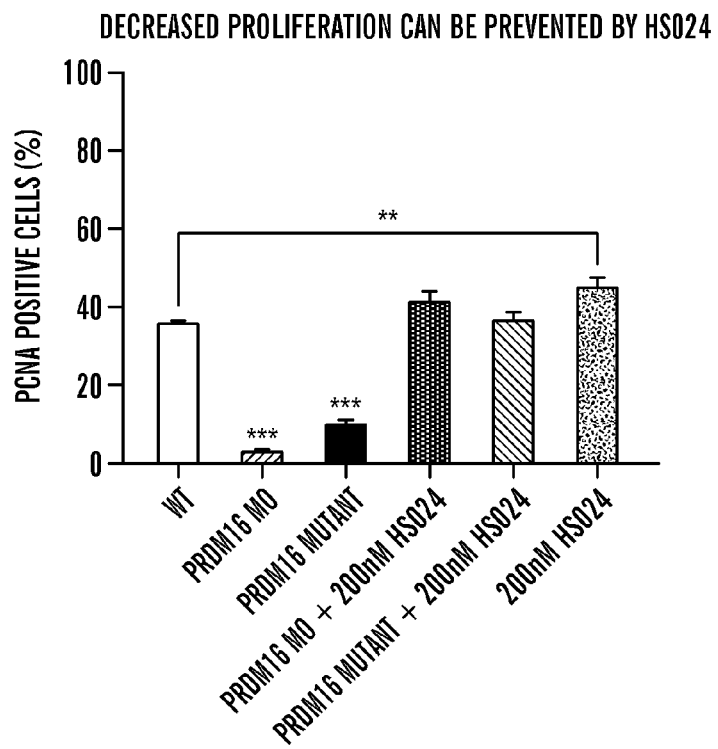
Figure 3E:
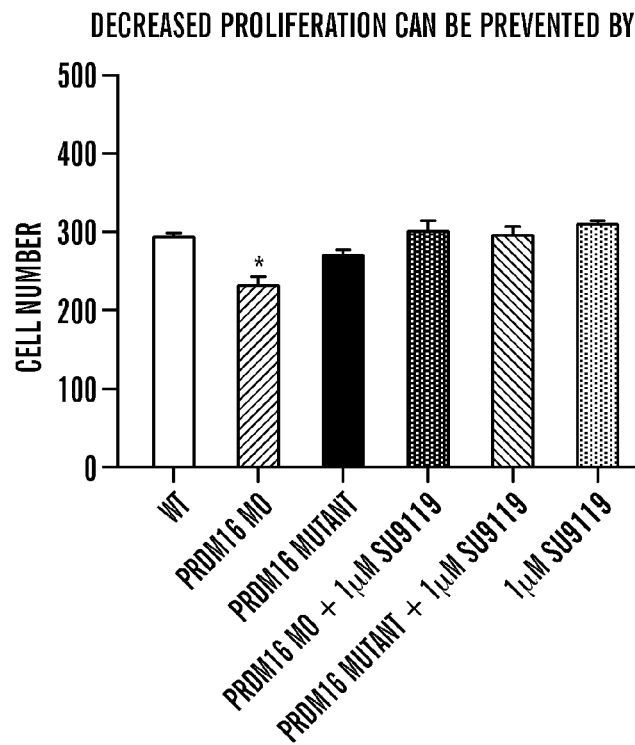
Figure 3F:
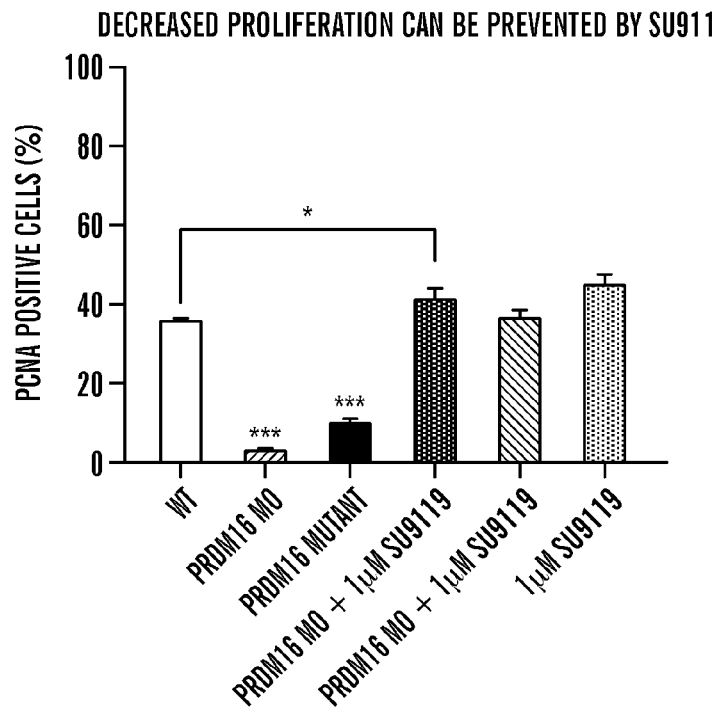
Figure 3G:
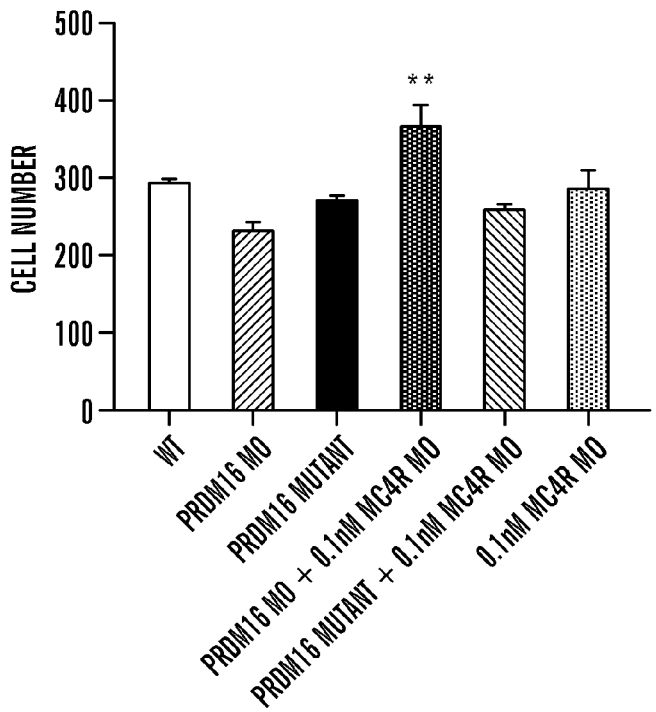
Figure 3H:
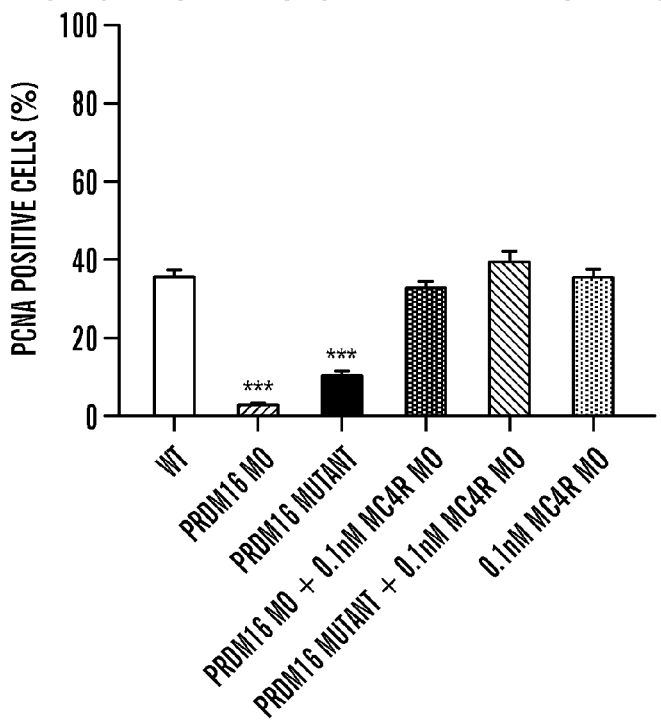
Figure 3I:
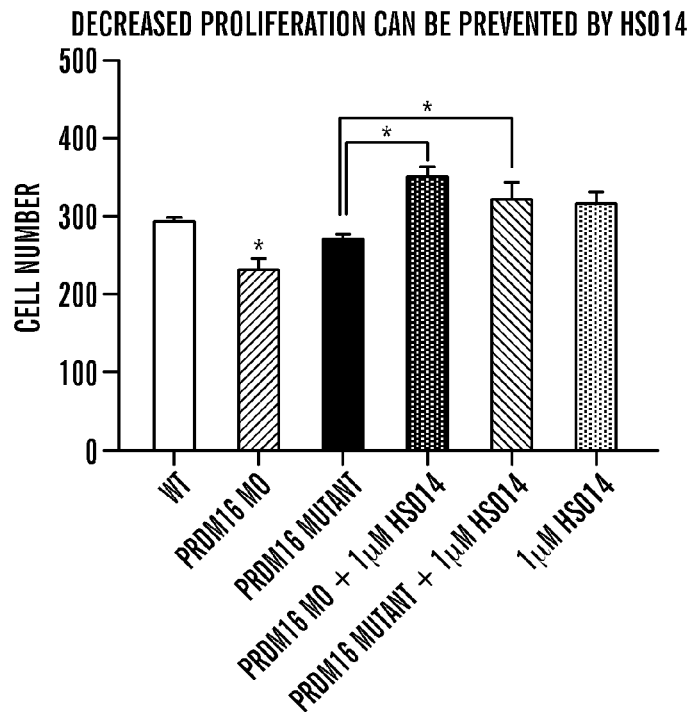
Figure 3J:
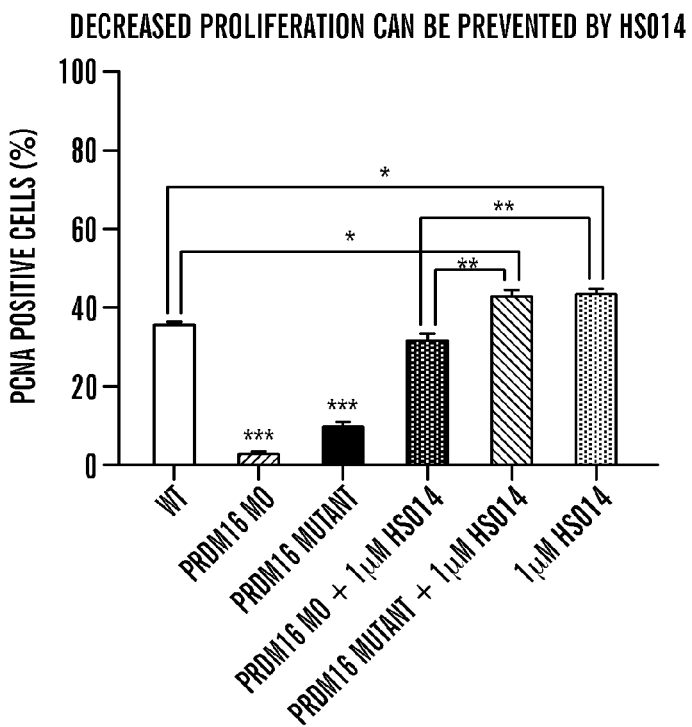
Figure 3K:
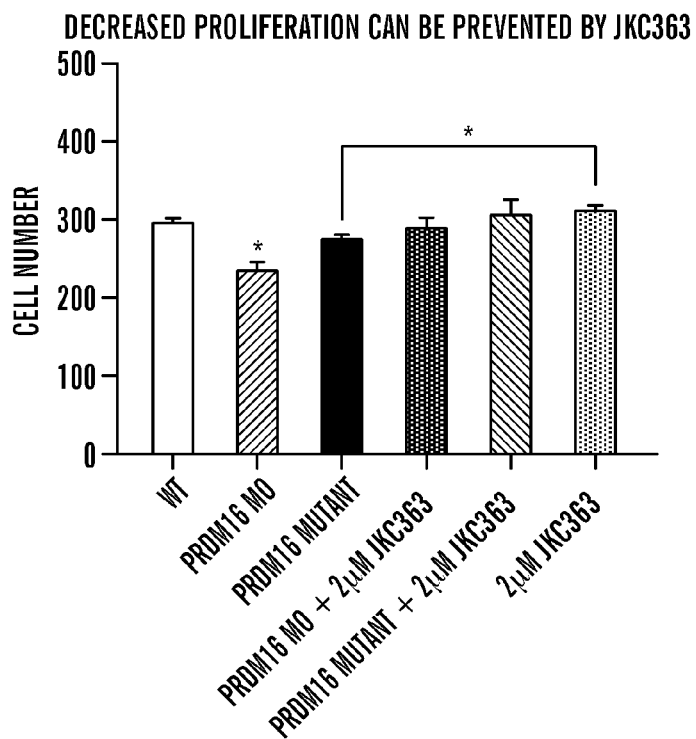
Figure 3L:
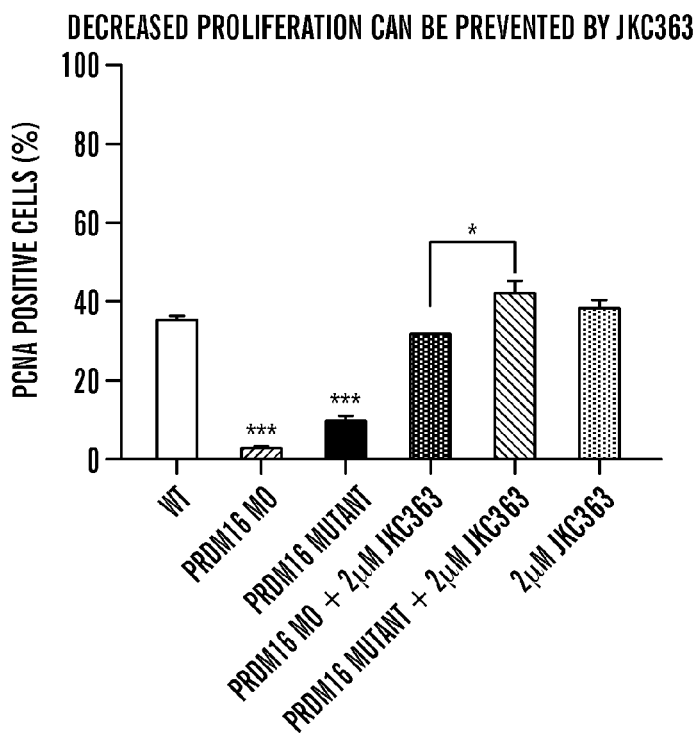
Figure 4A:
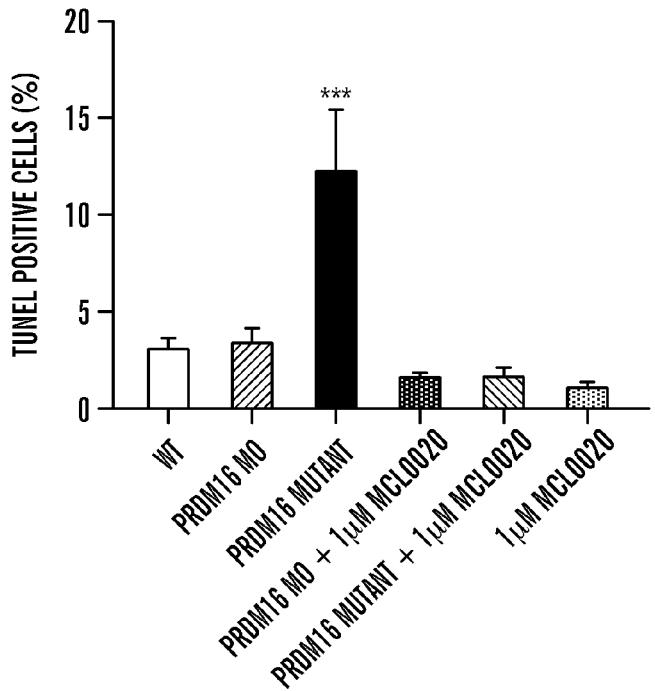
FIGS. 4A-4F are bar graph showing increased apoptosis can be restored with MCR4 antagonists MCL00200 (FIG. 4A), HS014 (FIG. 4B), JKC363 (FIG. 4C), SU9119 (FIG. 4D), MO (FIG. 4E), and HS024 (FIG. 4F).
Figure 4B:
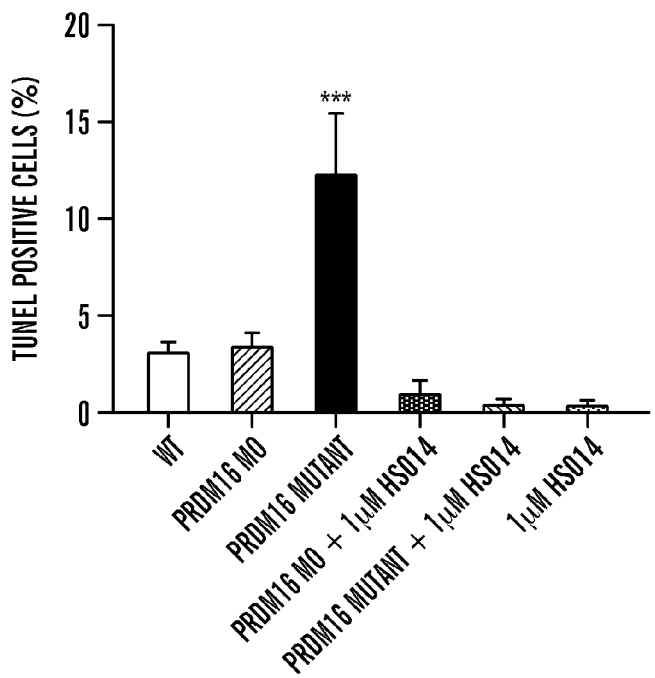
Figure 4C:
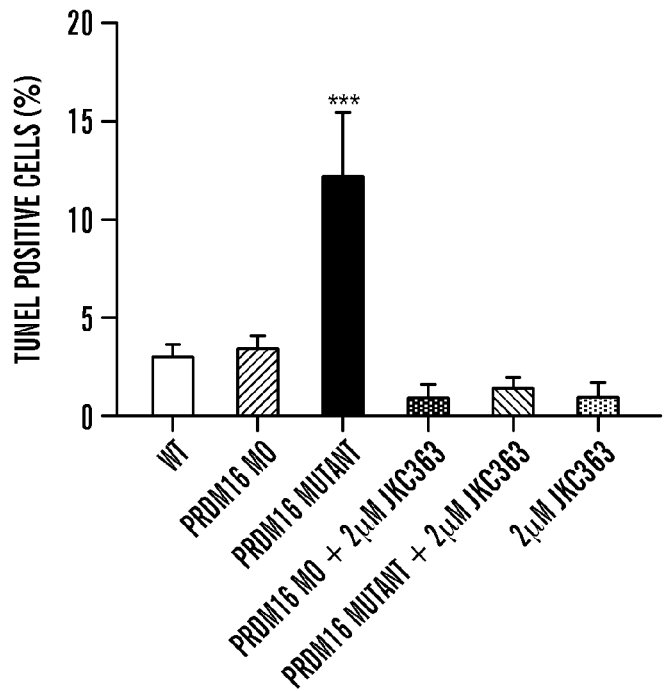
Figure 4D:
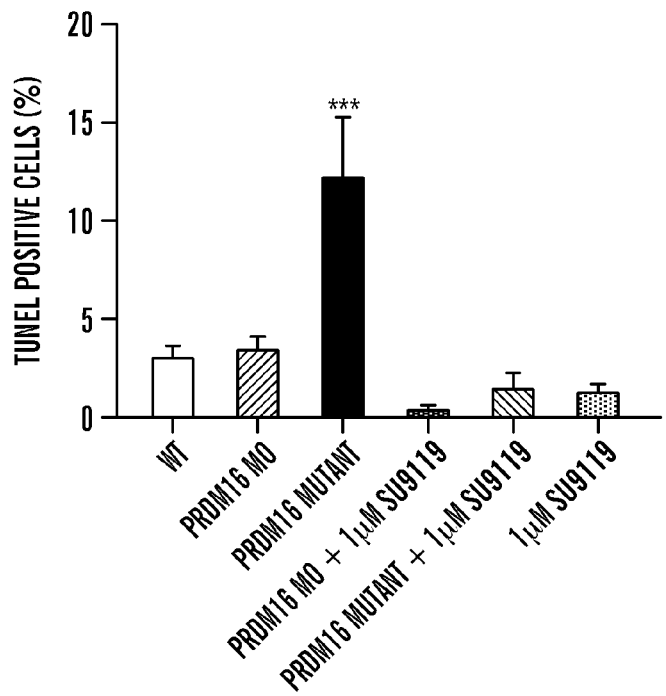
Figure 4E:
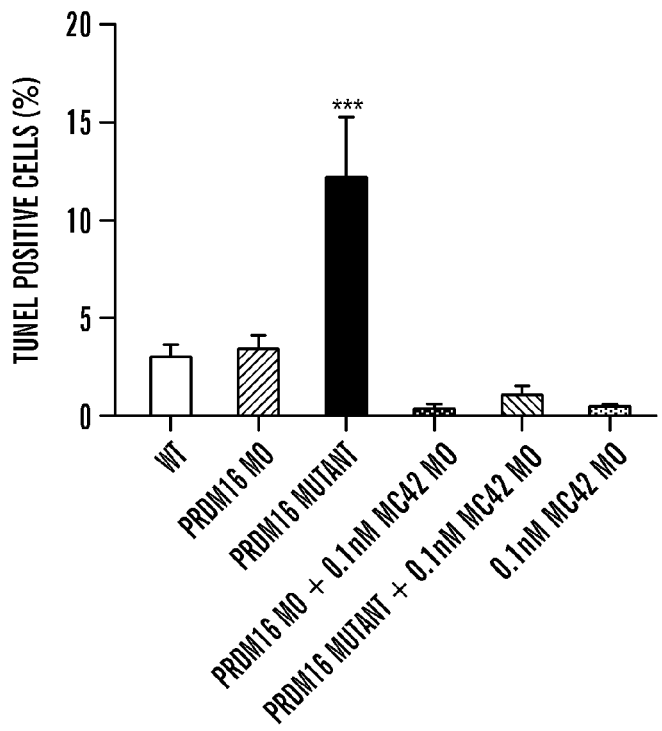
Figure 4F:
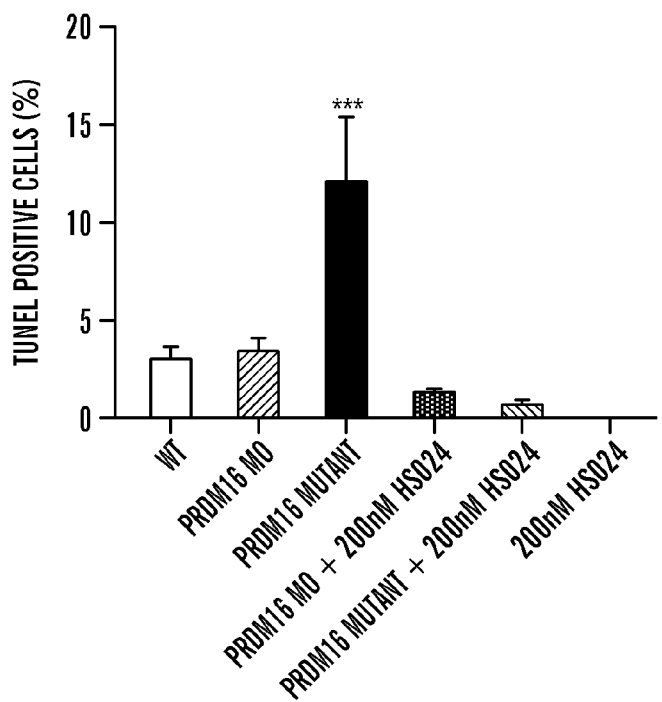
Figure 5:
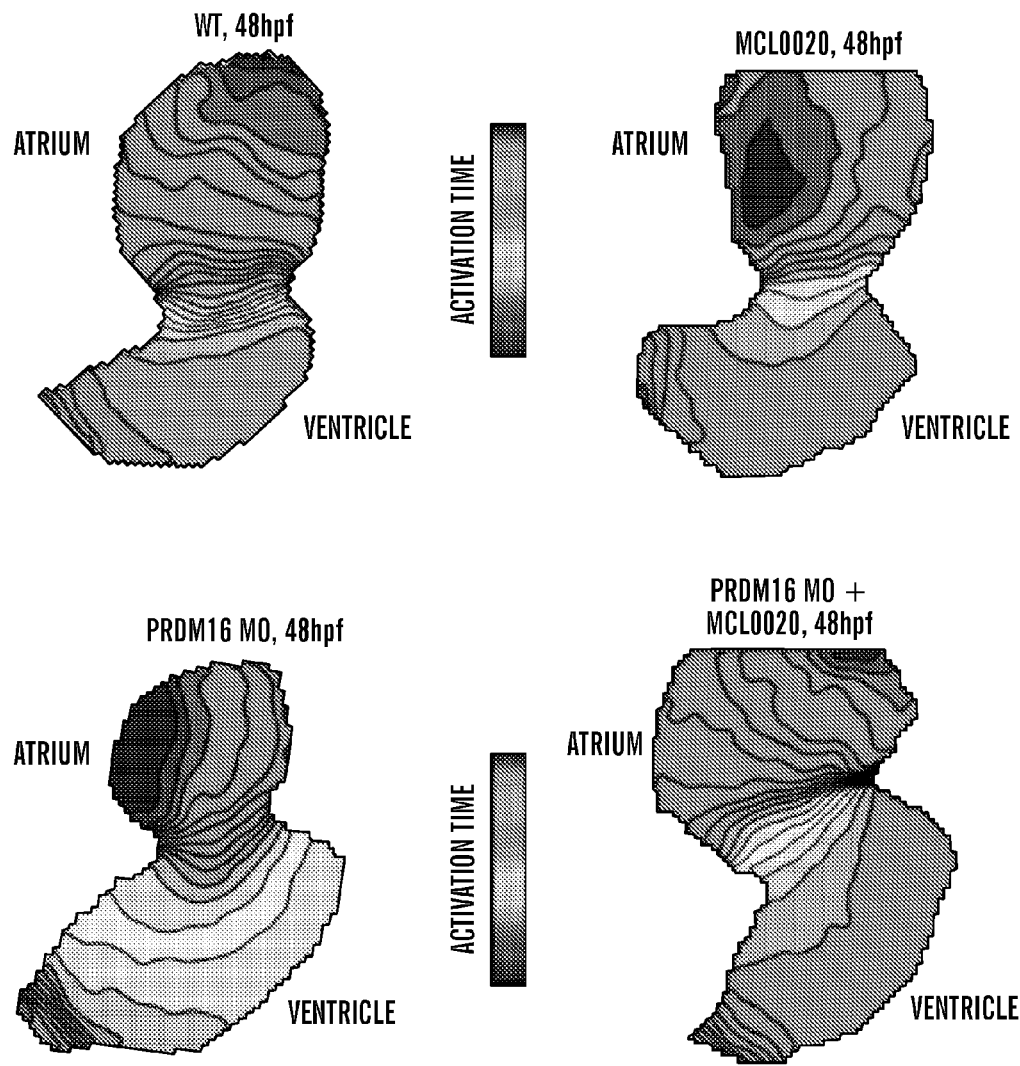
FIG. 5 shows maps of action potential wavefront of isolated hearts Grey scale depicts timing of electrical activation (dark grey areas activated before white areas).
Figure 6A:
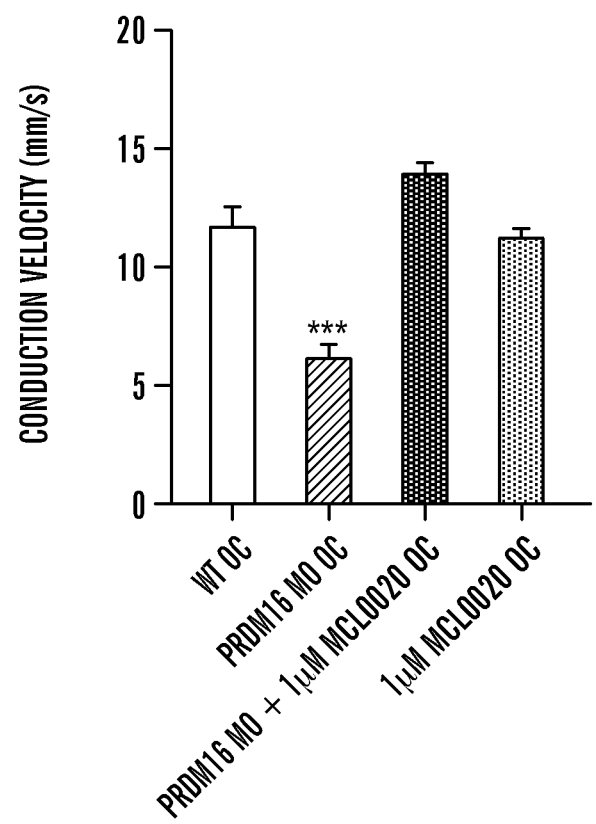
FIGS. 6A-6F are bar graph showing disrupted coupling of cells can be rescued with MCR4 antagonists MCL00200 (FIG. 6A), HS014 (FIG. 6B), SU9119 (FIG. 6C), JKC363 (FIG. 6D), HS024 (FIG. 6E), and MO (FIG. 6F).
Figure 6B:
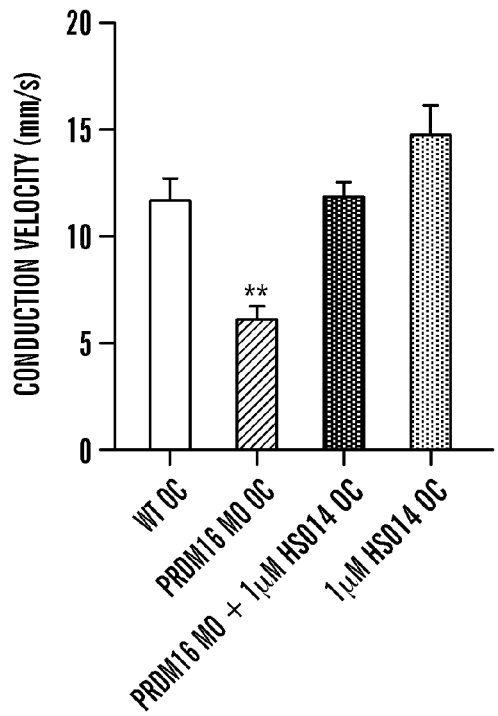
Figure 6C:
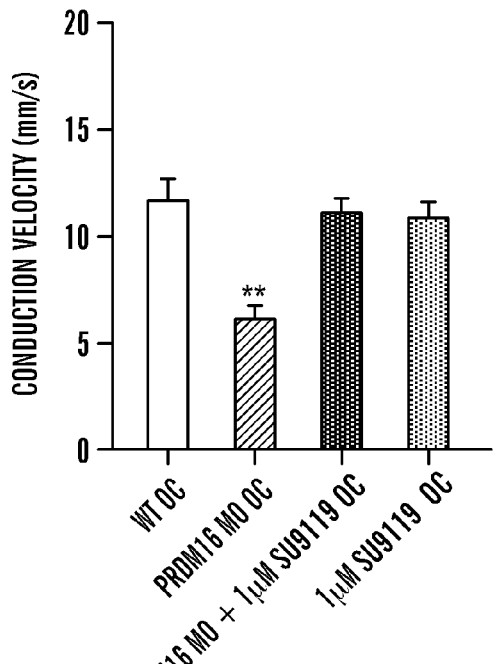
Figure 6D:
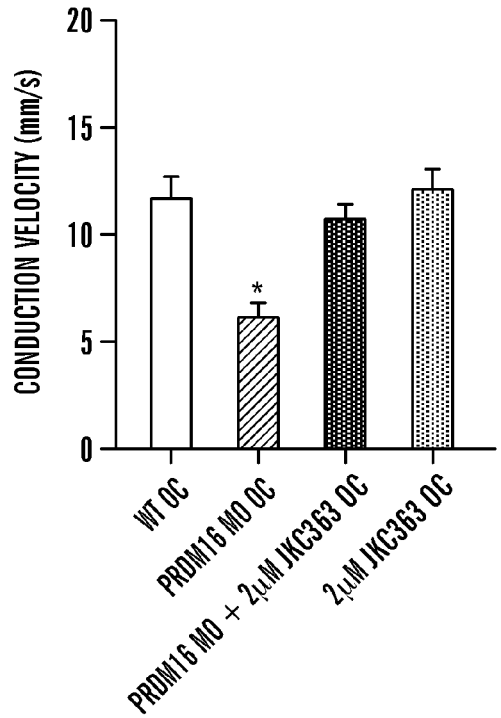
Figure 6E:
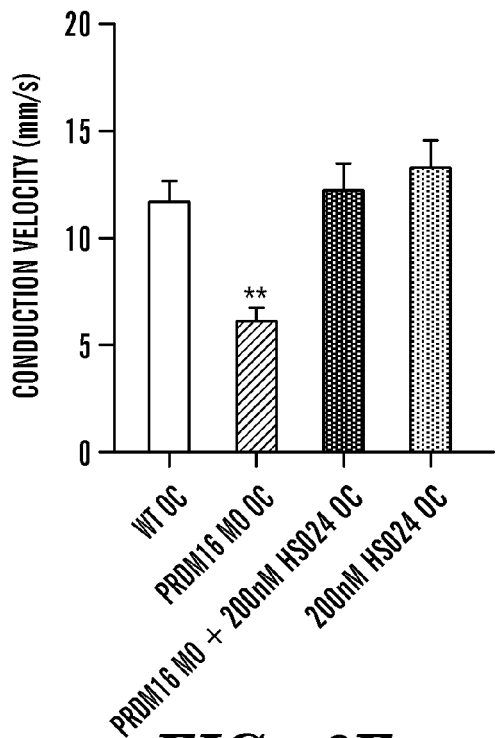
Figure 6F:
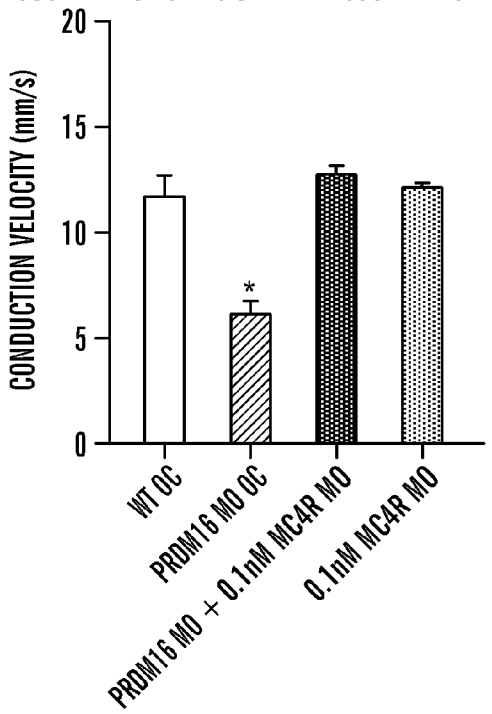
Figure 7:
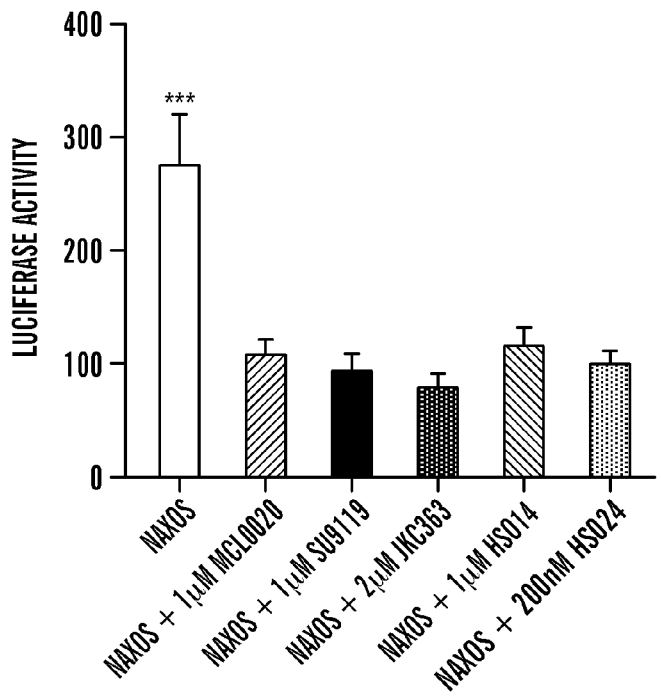
FIG. 7 is a bar graph showing heart failure in a zebrafish model of arrhythmogenic right ventricular cardiomyopathy (ARVC) can also be rescued with MCR4 antagonists.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

The various aspects disclosed herein are based, in part, on inventors' discovery that melanocortin receptor (MCR) antagonists, such as melanocortin receptor four (MC4R) antagonists, can rescue cardiomyopathy. Accordingly, in one aspect, the disclosure provides novel therapy for treating left ventricular non-compaction and/or dilated cardiomyopathy and/or arrhythmogenic right ventricular cardiomyopathy. Generally, the method comprises administering a therapeutically effective amount of a MCR antagonist to a subject in need thereof. In some embodiments, the MCR antagonist is a MC4R antagonist.

Melanocortins are involved in a wide range of physiological processes, including memory and/or learning, thermoregulation, analgesia, regulation of cardiovascular and immune systems and feeding behavior. Melanocortins exert their biological effects by binding to specific melanocortin receptors. There are five differentially expressed melanocortin receptors: MC1R, MC2R, MC3R, MC4R and MC5R. MC4R is predominantly expressed in the brain areas such as the cortex, hippocampus, amygdala, septal region, corpus striatum, thalamus, hypothalamus and brainstem.

MC4R is a 332 amino acid protein. There may be variations of sequences of MC4R when comparing MC4R of different organisms. Antagonists of one or more mammalian varieties of MC4R can be used according to embodiments of the various aspects disclosed herein to treat LVNC, DC or ARVC. Many functions have been attributed to MC4R including erectile dysfunction, nociception, food intake and energy expenditure.

As used herein, the term "MCR antagonist" refers not only to an agent that can act by directly inhibiting the normal function of a melanocortin receptor, but also to any agent that inhibits the melanocortin receptor pathway. Accordingly, as used herein, the term "MC4R antagonist" refers not only to any agent that can act by directly inhibiting the normal function of a melanocortin-4 receptor, but also to any agent that inhibits the melanocortin-4 receptor pathway. As used herein, MCR antagonists include reverse agonists of MCRs Without limitations, the MCR antagonists can be selected from the group consisting of peptides, peptide analogs and derivatives, peptidomimetics, proteins, small organic or inorganic molecules, antibodies, antigen or epitope binding fragments of antibodies, nucleic acids, nucleic acid analogs and derivatives, an extract made from biological materials, and any combinations thereof. In some embodiments, the antagonist is a peptide or analogs or derivative thereof. In some embodiments, the antagonist is a small molecule. In some embodiments, the antagonist is a nucleic acid molecule (including, e.g., but not limited to, siRNA, antisense, aptamer, ribozymes, and combinations thereof). In some embodiments, the nucleic acid-based antagonist can comprise one or more nucleotide modifications. In some embodiments where the antagonist is a nucleic acid molecule, the antagonist can be designed to target at least a portion of the MCR4 or MC4R gene and/or mRNA.

Exemplary MCR antagonists include, but are not limited to, Compound 10, Pontillo14c, Compound 10d, Compound 18v, Compound 13b-2, Compound Tran12e, and Compounds Xi14a-j, as described in US20100129319, substituted 1-benzyl-4-aryl piperazine and piperidine analogues, as described in US2005/0065162; substituted benzimidazole analogues, as described in US2003/0229074; and antagonists described in US2003/0216390, US2003/0077701, U.S. Pat. No. 6,569,861, U.S. Pat. No. 6,693,165, U.S. Pat. No. 8,236,818, WO 03/035055, WO 03/033480, WO 03/033476, WO 03/015769, WO 03/028641, WO 03/013574, WO 03/004027, WO 02/094799, WO 02/089729, WO 02/083134, WO 02/068387, WO 02/076947, WO 02/076929, WO 02/057233, WO 02/051809, WO 02/10146, WO 02/067869, EP1468999, EP1460070, EP1974729, EP2439197, EP1940401, PCT/EP2007/003115, PCT/EP2007/001595, PCT/EP2004/002907, PCT/EP2004/002896, PCT/EP2004/002908, PCT/EP2004/002909, PCT/US2002/032282, PCT/US2003/004455, PCT/US2003/014628, PCT/US2003/040931, PCT/US2004/035343, PCT/US2004/034951, PCT/US2002/023926, PCT/US2002/023616, content of all of which is incorporated herein by reference in their entireties. It will be apparent that the above are illustrative examples of MCH receptor antagonists, and are not intended to limit the scope of the present invention.

In some embodiments, the MCR antagonist is selected from the group consisting of:

(MCL0020, SEQ ID NO: 1)
Ac-D-2-Nal-Arg-2-Nal-NH$_2$, (SHU9119, SEQ ID NO: 2)
Ac-Nle-cyclo(Asp-His-D-2-Nal-Arg-Trp-Lys)-NH$_2$, (HS014, SEQ ID NO: 3)
Ac-Cys-Glu-His-D-2-Nal-Arg-Trp-Gly-Cys-Prol-Pro-Lys-Asp-NH$_2$, (HS024, SEQ ID NO: 4)
Ac-Cys-Nle-Arg-His-D-Nal-Arg-Trp-Gly-Cys-NH$_2$, (JKC363, SEQ ID NO: 5)
Mpr-Glu-His-D-2-Nal-Arg-Trp-Gly-Cys-Pro-Pro-Lys-Asp-NH$_2$, Ac-Cys-Glu-His-(diCl-D-Phe)-Arg-Trp-Gly-Cys-Pro-Pro-Lys-Asp-NH$_2$, wherein diCl-D-Phe is a dichloro-D-phenylalanine (HS028, SEQ ID NO: 6); HS131, BL-6020/979, MCL0129, MPB-10, MCL-0042, MCL-0129, Agouti-related peptides (e.g., Agouti 1-40 and Agouti 87-132), and any combinations thereof.

In some embodiments, the MCR antagonist is selected from the group consisting of MCL0020, SHU9119, HS014, HS024, JKC36, and any combinations thereof.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with autoimmune disease or inflammation. In addition, the methods and compositions described herein can be used to treat domesticated animals and/or pets.

A subject can be one who has been previously diagnosed with or identified as suffering from LVNC or DC or ARVC. A subject can be one who is currently being treated for LVNC or DC or ARVC.

In some embodiments, the method comprises a step of selecting a subject for treatment. For example, the selecting can be diagnosing the subject for left ventricular non-compaction cardiomyopathy or dilated cardiomyopathy or arrhythmogenic right ventricular cardiomyopathy before onset of treatment with the method described herein. Methods for diagnosing LVNC, DC and ARVC are well known in the art and readily available to one of skill in the art. The diagnosis of LVNC is based on cardiac testing, family history, medical history, and physical exam. An echocardiogram is the most common test used to diagnose LVNC, as the trabeculations within the left ventricle and overall squeeze of the heart can be measured with this test. Trabeculation of the ventricles is normal, as are prominent, discrete muscular bundles greater than 2 mm. In non-compaction there is excessively prominent trabeculations. Chin et al. (1990), *Circulation* 82 (2): 507-13 described echocardiographic method to distinguish non-compaction from normal trabeculation. They described a ratio of the distance from the trough and peak, of the trabeculations, to the epicardial surface. Non-compaction is diagnosed when the trabeculations are more than twice the thickness of the underlying ventricular wall. A family tree can be constructed with specific attention to cardiomyopathy, rhythm problems, sudden cardiac or unexplained death, cardiac surgery or presence of other cardiac disease in relatives. A history of heart failure symptoms including feeding issues, heart rhythm problems and exercise intolerance can be indication of LVNC. LVNC can also be diagnosed by a thorough physical exam to evaluate for signs of a cardiac problem. Assessment of skeletal muscle strength can also be performed since problems with skeletal muscle may occur with cardiac muscle disease. Many individuals with LVNC experience no symptoms. For those who have heart failure or an abnormal heart rhythm, symptoms can include: shortness of breath and fatigue, feeling dizzy or light-headed, fainting or passing out (syncope), feeling abnormal heart beats (palpitations), or unexplained weight gain or swelling.

Signs and symptoms of dilated cardiomyopathy include, but are not limited to fatigue; shortness of breath (dyspnea) when active or lying down; reduced ability to exercise; swelling (edema) in legs, ankles and feet; swelling of abdomen (ascites). Generalized enlargement of the heart is seen upon normal chest X-ray. Pleural effusion may also be noticed, which is due to pulmonary venous hypertension. The electrocardiogram often shows sinus tachycardia or atrial fibrillation, ventricular arrhythmias, left atrial enlargement, and sometimes intraventricular conduction defects and low voltage. When left bundle-branch block (LBBB) is accompanied by right axis deviation (RAD), the rare combination is considered to be highly suggestive of dilated or congestive cardiomyopathy. (Nikolic G, Marriott H J (October 1985). "Left bundle branch block with right axis deviation: a marker of congestive cardiomyopathy". J Electrocardiol 18 (4): 395-404. doi:10.1016/s0022-0736(85)80022-4 and Childers R, Lupovich S, Sochanski M, Konarzewska H. (2000). "Left bundle branch block and right axis deviation: a report of 36 cases". J Electrocardiol 33 (Suppl): 93-102. doi:10.1054/jcic.2000.20326) Echocardiogram shows left ventricular dilatation with normal or thinned walls and reduced ejection fraction. Cardiac catheterization and coronary angiography are often performed to exclude ischemic heart disease. Genetic testing can be important, since one study has shown that gene mutations in the TTN gene (which codes for a protein called titin) are responsible for "approximately 25% of familial cases of idiopathic dilated cardiomyopathy and 18% of sporadic cases." (Herman et al., (Feb. 16, 2012). "Truncations of Titin causing dilated cardiomyopathy". N Engl J Med 366 (7): 619-628) The results of the genetic testing can help the doctors and patients understand the underlying cause of the dilated cardiomyopathy. Genetic test results can also help guide decisions on whether a patient's relatives should undergo genetic testing (to see if they have the same genetic mutation) and cardiac testing to screen for early findings of dilated cardiomyopathy. Cardiac magnetic resonance imaging (cardiac MM) may also provide helpful diagnostic information in patients with dilated cardiomyopathy. (Pennell et al., (November 2004), "Clinical indications for cardiovascular magnetic resonance (CMR): Consensus Panel report" Eur Heart J 25 (21): 1940-1965)

ARVC can be diagnosed using a number of different clinical tests, such as, but not limited to, electrocardiogram (EKG), echocardiography, right ventricular angiography, cardiac MRI, and genetic testing. About 90% of individuals with ARVC have some EKG abnormality. The most common EKG abnormality seen in ARVC is T wave inversion in leads V1 to V3. However, this is a non-specific finding, and may be considered a normal variant in right bundle branch block (RBBB), women, and children under 12 years old. RBBB itself is seen frequently in individuals with ARVC. This may be due to delayed activation of the right ventricle, rather than any intrinsic abnormality in the right bundle branch.

The epsilon wave is found in about 50% of those with ARVC. This is described as a terminal notch in the QRS complex. It is due to slowed intraventricular conduction. The epsilon wave may be seen on a surface EKG; however, it is more commonly seen on signal averaged EKGs. Ventricular ectopy seen on a surface EKG in the setting of ARVD is typically of left bundle branch block (LBBB) morphology, with a QRS axis of −90 to +110 degrees. The origin of the ectopic beats is usually from one of the three regions of fatty degeneration (the "triangle of dysplasia"): the RV outflow tract, the RV inflow tract, and the RV apex. Signal averaged ECG (SAECG) can be used to detect late potentials and epsilon waves in individuals with ARVD.

Echocardiography can reveal an enlarged, hypokinetic right ventricle with a paper-thin RV free wall. The dilatation of the RV will cause dilatation of the tricuspid valve annulus, with subsequent tricuspid regurgitation. Paradoxical septal motion may also be present.

Fatty infiltration of the RV free wall can be visible on cardiac MM. Fat has increased intensity in T1-weighted images. However, it may be difficult to differentiate intramyocardial fat and the epicardial fat that is commonly seen adjacent to the normal heart. Also, the sub-tricuspid region may be difficult to distinguish from the atrioventricular sulcus, which is rich in fat. Cardiac MRI can visualize the extreme thinning and akinesis of the RV free wall. However, the normal RV free wall may be about 3 mm thick, making the test less sensitive.

Right ventricular angiography is considered the gold standard for the diagnosis of ARVC. Findings consistent with ARVC are an akinetic or dyskinetic bulging localized to the infundibular, apical, and subtricuspid regions of the RV. The specificity is 90%; however, the test is observer dependent.

Transvenous biopsy of the right ventricle can be highly specific for ARVC, but it has low sensitivity. False positives include other conditions with fatty infiltration of the ventricle, such as chronic alcohol abuse and Duchenne/Becker muscular dystrophy. False negatives are common, however, because the disease progresses typically from the epicardium to the endocardium (with the biopsy sample coming from the endocardium), and the segmental nature of the disease. Also, due to the paper-thin right ventricular free wall that is common in this disease process, most biopsy samples are taken from the ventricular septum, which is commonly not involved in the disease process. A biopsy sample that is consistent with ARVC would have >3% fat, >40% fibrous tissue, and <45% myocytes.

ARVC is an autosomal dominant trait with reduced penetrance. Approximately 40-50% of ARVC patients have a mutation identified in one of several genes encoding components of the desmosome, which can help confirm a diagnosis of ARVC. (Sen-Chowdhry S, Syrris P, McKenna W J (November 2007). "Role of genetic analysis in the management of patients with arrhythmogenic right ventricular dysplasia/cardiomyopathy". J. Am. Coll. Cardiol. 50 (19): 1813-21.) Since ARVD is an autosomal dominant trait, children of an ARVD patient have a 50% chance of inheriting the disease causing mutation. Whenever a mutation is identified by genetic testing, family-specific genetic testing can be used to differentiate between relatives who are at-risk for the disease and those who are not. ARVD genetic testing is clinically available.

There is no pathognomonic feature of ARVC. The diagnosis of ARVC is based on a combination of major and minor criteria. To make a diagnosis of ARVC requires either 2 major criteria or 1 major and 2 minor criteria or 4 minor criteria. Major criteria include right ventricular dysfunction (e.g., severe dilatation and reduction of RV ejection fraction with little or no LV impairment, localized RV aneurysms, and severe segmental dilatation of the RV), tissue characterization (e.g., fibrofatty replacement of myocardium on endomyocardial biopsy), conduction abnormalities (e.g., epsilon waves in V1-V3 and localized prolongation (>110 ms) of QRS in V1-V3), and family history (e.g., familial disease confirmed on autopsy or surgery). Minor criteria include right ventricular dysfunction (e.g., mild global RV dilatation and/or reduced ejection fraction with normal LV, mild segmental dilatation of the RV, and regional RV hypokinesis) tissue characterization, conduction abnormalities (e.g., inverted T waves in V2 and V3 in an individual over 12 years old, in the absence of a right bundle branch block (RBBB), late potentials on signal averaged EKG, ventricular tachycardia with a left bundle branch block (LBBB) morphology, and frequent PVCs (>1000 PVCs/24 hours)), and family history (e.g., family history of sudden cardiac death before age 35 and family history of ARVC).

Inventors have also discovered inter alia that MCR antagonists, such as MC4R antagonists are particularly effective for treating LVNC or DC in subjects having one or more mutations in PRDM 16 gene. Previous work from the inventors showed that mutations in the PRDM 16 gene can be a cause of syndromic and non-syndromic left ventricular non-compaction and cardiomyopathy. (Arndt et al., American Journal of Human Genetics, (2013) Volume 93, Issue 1, p67-77) Now the inventors have discovered that MCR antagonists, such as MC4R antagonists, are particularly useful in rescuing the deleterious effects of mutations in the PRDM16 gene. Accordingly, in some embodiments, the subject has a mutation in the PR domain containing 16 (PRDM 16) gene. In some embodiments, the method comprises a step of selecting a subject having a mutation in the PRDM16 gene.

Without limitations, the mutation can be a truncation, frameshift, or missense mutation. In some embodiments, the mutation in the PRDM16 gene is selected from the group consisting of a mutation associated with left ventricular non-compaction and dilated cardiomyopathy. In some embodiments, the mutation in the PRDM16 gene can be selected from any of the mutations listed in Table 1 below.

| Disease | Variant | Nucleotide change | Mutation | Exon | Affected individual |
|---|---|---|---|---|---|
| DCM | p.Glu271Lys | c.811G > A | missense | 6 | 1 |
| DCM | p.Pro291Leu | c.872C > T | missense | 6 | 1 |
| LVNC | p.Arg525Profs*79 | c.1573dupC | frameshift | 9 | 1 |
| LVNC | p.Lys702* | c.2104A > T | truncation | 9 | 1 |
| LVNC | p.Asn816Ser | c.2447A > G | missense | 9 | 1 |
| DCM | p.Leu887Pro | c.2660T > C | missense | 10 | 1 |
| DCM | p.Val2202Met | c.3301G > A | missense | 15 | 2 |

In some embodiments, the method further comprises a step of assaying a sample, such as a biological sample, from the subject to determine if the subject has a mutation in the PRDM16 gene. The term "biological sample" as used herein denotes a sample taken or isolated from a biological organism, e.g., tissue cell culture supernatant, cell lysate, a homogenate of a tissue sample from a subject or a fluid sample from a subject. Exemplary biological samples include, but are not limited to, blood, sputum, urine, spinal fluid, pleural fluid, nipple aspirates, lymph fluid, the external sections of the skin, respiratory, intestinal, and genitourinary tracts, tears, saliva, milk, feces, sperm, cells or cell cultures, serum, leukocyte fractions, smears, tissue samples of all kinds, embryos, etc. . . . . The term also includes both a mixture of the above-mentioned samples as well as food samples that contain free or bound nucleic acids or cells containing nucleic acids. The term "biological sample" also includes untreated or pretreated (or pre-processed) biological samples.

A "biological sample" can contain cells from subject, but the term can also refer to non-cellular biological material, such as non-cellular fractions of blood, saliva, or urine, that can be used to measure mutations or gene expression levels of PRDM16. In some embodiments, the sample is from a resection, biopsy, or core needle biopsy. In addition, fine needle aspirate samples can be used. Samples can be either paraffin-embedded or frozen tissue. The sample can be obtained by removing a sample of cells from a subject, but can also be accomplished by using previously isolated cells (e.g. isolated by another person). In addition, the biological sample can be freshly collected or a previously collected sample.

In some embodiments, biological sample can be a biological fluid. Examples of biological fluids include, but are not limited to, saliva, bone marrow, blood, serum, plasma, urine, sputum, cerebrospinal fluid, an aspirate, tears, and any combinations thereof.

In some embodiments, the biological sample is an untreated biological sample. As used herein, the phrase "untreated biological sample" refers to a biological sample that has not had any prior sample pre-treatment except for dilution and/or suspension in a solution. Exemplary methods for treating a biological sample include, but are not limited to, centrifugation, filtration, sonication, homogenization, heating, freezing and thawing, and any combinations thereof.

In some embodiments, the biological sample is a frozen biological sample, e.g., a frozen tissue or fluid sample such as urine, blood, serum or plasma. The frozen sample can be thawed before employing methods, assays and systems of the invention. After thawing, a frozen sample can be centrifuged before being subjected to methods, assays and systems of the invention.

In some embodiments, the biological fluid sample can be treated with at least one chemical reagent, such as a protease inhibitor. In some embodiments, the biological fluid sample is a clarified biological fluid sample, for example, by centrifugation and collection of a supernatant comprising the clarified biological fluid sample.

In some embodiments, a biological sample is a pre-processed biological sample, for example, supernatant or filtrate resulting from a treatment selected from the group consisting of centrifugation, filtration, sonication, homogenization, lysis, thawing, amplification, purification, restriction enzyme digestion ligation and any combinations thereof. In some embodiments, a biological sample can be a nucleic acid product amplified after polymerase chain reaction (PCR). The term "nucleic acid" used herein refers to DNA, RNA, or mRNA.

In some embodiments, the biological sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. In addition, or alternatively, chemical and/or biological reagents can be employed to release nucleic acid or protein from the sample.

The skilled artisan is well aware of methods and processes appropriate for pre-processing of biological samples required for determination of gene mutations.

Methods of determining mutations in a gene are well known in the art and readily available to one of skill in the art. For example, mutations can be detected directly or indirectly using any of a variety of suitable methods including fluorescent polarization, mass spectroscopy, and the like. Suitable methods comprise direct or indirect sequencing methods, restriction site analysis, hybridization methods, nucleic acid amplification methods, gel migration methods, the use of antibodies that are specific for the proteins encoded by the different mutated genes or by other suitable means. Alternatively, many such methods are well known in the art and are described, for example in T. Maniatis et al., Molecular Cloning, a Laboratory Manual, 4$^{th}$ Edition, Cold Spring Harbor Press, Cold Spring Harbor, N.Y. (2012), J. W. Zyskind et al., Recombinant DNA Laboratory Manual, Academic Press, Inc., New York (1988), and in R. Elles, Molecular Diagnosis of Genetic Diseases, Humana Press, Totowa, N.J. (1996), and Mamotte et al, 2006, Clin Biochem Rev, 27; 63-75) each herein incorporated by reference.

Without limitations, any approach that detects mutations or polymorphisms in a gene can be used, including but not limited to single-strand conformational polymorphism (SSCP) analysis (Orita et al. (1989) Proc. Natl. Acad. Sci. USA 86:2766-2770), heteroduplex analysis (Prior et al. (1995) Hum. Mutat. 5:263-268), oligonucleotide ligation (Nickerson et al. (1990) Proc. Natl. Acad. Sci. USA 87:8923-8927) and hybridization assays (Conner et al. (1983) Proc. Natl. Acad. Sci. USA 80:278-282). Traditional Taq polymerase PCR-based strategies, such as PCR-RFLP, allele-specific amplification (ASA) (Ruano and Kidd (1989) Nucleic Acids Res. 17:8392), single-molecule dilution (SMD) (Ruano et al. (1990) Proc. Natl. Acad. Sci. USA 87:6296-6300), and coupled amplification and sequencing (CAS) (Ruano and Kidd (1991) Nucleic Acids Res. 19:6877-6882), contents of all of which is incorporated herein by reference.

For administration to a subject, the MCR antagonists can be provided in pharmaceutically acceptable compositions. These pharmaceutically acceptable compositions comprise the antagonist, formulated together with one or more pharmaceutically acceptable carriers (additives) and/or diluents. As described in detail below, the pharmaceutical compositions of the present invention can be specially formulated for administration in solid or liquid form, including those adapted for the following: (1) oral administration, for example, drenches (aqueous or non-aqueous solutions or suspensions), gavages, lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, antagonists can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 3,270,960, content of all of which is herein incorporated by reference.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

In some embodiments, the pharmaceutical composition comprises a pharmaceutically acceptable carrier or excipient and a peptide selected from the group consisting of:

Ac-D-2-Nal-Arg-2-Nal-NH$_2$, (SEQ ID NO: 1)

Ac-Nle-cyclo(-Asp-His-D-2-Nal-Arg-Trp-Lys)-NH$_2$, (SEQ ID NO: 2)

Ac-Cys-Glu-His-D-2-Nal-Arg-Trp-Gly-Cys-Prol-Pro-Lys-Asp-NH$_2$, (SEQ ID NO: 3)

Ac-Cys-Nle-Arg-His-D-Nal-Arg-Trp-Gly-Cys-NH$_2$, (SEQ ID NO: 4)

Mpr-Glu-His-D-2-Nal-Arg-Trp-Gly-Cys-Pro-Pro-Lys-Asp-NH$_2$, (SEQ ID NO: 5)

and any combinations thereof.

The phrase "therapeutically-effective amount" as used herein means that amount of a MCR antagonist, or composition comprising the antagonist, which is effective for producing some desired therapeutic effect in at least a sub-population of cells in an animal at a reasonable benefit/risk ratio applicable to a condition or a disease condition in which treatment is sought. For example, an amount of a MCR antagonist administered to a subject that is sufficient to produce a statistically significant, measurable desired therapeutic effect.

A therapeutically effective amount can be determined on an individual basis and will be based, at least in part, on consideration of the physiological characteristics of the mammal, the type of delivery system or therapeutic technique used and the time of administration relative to the progression of the disease. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

As used herein, the term "administer" refers to the placement of a composition into a subject by a method or route which results in at least partial localization of the composition at a desired site such that desired effect is produced. Routes of administration suitable for the methods disclosed herein include both local and systemic administration. Generally, local administration results in more of the composition being delivered to a specific location as compared to the entire body of the subject, whereas, systemic administration results in delivery to essentially the entire body of the subject.

The MCR antagonist can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration. Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments of the aspects described herein, the compositions are administered by intravenous infusion or injection.

"Transdermal" administration can be accomplished using a topical cream or ointment or by means of a transdermal patch. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions can be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the parenteral route, the compositions can be in the form of solutions or suspensions for infusion or for injection. Via the topical route, the pharmaceutical compositions based on compounds according to the invention can be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication. Via the ocular route, they may be in the form of eye drops.

The pharmaceutical composition can also be encapsulated, tableted or prepared in an emulsion or syrup for oral administration. Pharmaceutically acceptable solid or liquid carriers can be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The amount of an MCR antagonist that can be combined with a carrier material to produce a single dosage form will generally be that amount of the MCR antagonist that produces a therapeutic effect. Generally out of one hundred percent, this amount will range from about 0.01% to 99% of antagonist, preferably from about 5% to about 70%, most preferably from 10% to about 30%.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred.

As used herein, the term ED denotes effective dose and is used in connection with animal models. The term EC denotes effective concentration and is used in connection with in vitro models.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage can be determined by a physician and adjusted, as necessary, to suit observed effects of the treatment. Generally, the compositions are administered so that RARγ agonist is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 tmg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In some embodiments, the antagonists are administered at a dosage so that the antagonist or a metabolite thereof has an in vivo concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05, less than 0.01, nM, less than 0.005 nM, less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered every day or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

In some embodiments, the pharmaceutical composition further comprises one or more additional therapeutically active ingredients (e.g., LVNC or DC management therapy agent and/or palliative). As used herein, the term "palliative" refers to treatment that is focused on the relief of symptoms of a disease and/or side effects of a therapeutic regimen, but is not curative.

Combination Therapy

In some embodiments, a LVNC or DC management therapy can be co-administered with the MCR antagonist. For example, the MCR antagonist can be administered before, concurrently, or after administration of the LVNC or DC management therapy. Thus, as used herein, the term "co-administer" refers to administration of two or more therapies (e.g., the MCR antagonist and the LVNC or DC management therapy) within a 24 hour period of each other, for example, as part of a clinical treatment regimen. In other embodiments, "co-administer" refers to administration within 12 hours, within 6 hours, within 5 hours, within 4 hours, within 3 hours, within 2 hours, within 1 hour, within 45, within 30 minutes, within 20, within 15 minutes, within 10 minutes, or within 5 minutes of each other. In other embodiments, "co-administer" refers to administration at the same time, either as part of a single formulation or as multiple formulations that are administered by the same or different routes. When the MCR antagonist and the LVNC or DC management therapy are administered in different pharmaceutical compositions or at different times, routes of administration can be same or different.

Other therapies, imaging agents, and/or management therapy agents that can be used in combination with the MCR antagonists for imaging, targeting, detecting and/or treating LVNC or DC include pacemaker, biventricular pacing devices, left ventricular assist device, implantable cardioverter-defibrillator (ICD), heart bypass (CABG) surgery, angioplasty, valve replacement or repair, heart transplant or artificial heart implant.

It is appreciated that the MCR antagonists and pharmaceutical compositions comprising same can be formulated and employed in combination therapies, that is, the MCR antagonists and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It is appreciated that the therapies employed can achieve a desired effect for the same disorder (for example, an inventive compound can be administered concurrently with another LVNC or DC management therapy agent), or they can achieve different effects (e.g., control of an adverse effects).

For example, other therapies, imaging agents, and/or management therapy agents that can be used in combination with the MCR antagonists for imaging, targeting, detecting and/or treating LVNC or DC include angiotensin-converting enzyme (ACE), such as benazepril (Lotensin), captopril (Capoten), enalapril (Vasotec), fosinopril (Monopril) lisinopril (Zestril, Prinivil), perindopril (Aceon), quinapril (Accupril), ramipril (Altace) and trandolpril (Mavik); angiotensin receptor blockers (ARBs), such as candesartan (Atacand), eprosartan (Teveten), losartan (Cozaar) irbesartan (Avapro), olmesartan (Benicar), telmisartan (Micardis) and valsartan (Diovan); beta blockers, such as acebutolol (Sectral), atenolol (Temormin), betaxolol, carvedilol (Coreg) labetalol (Trandate), metoprolol (Lopressor, Toprol-XL), nadolol (Corgard), penbutolol (Levatol) and pinodol; cardiac glycosides, such as digoxin (digitalis) (Lanoxin); diuretics such as bumetanide (Bumex) and furosemide (Lasix), and steroidal antimineralocorticoid agent such as spironolactone (Aldactone), beta-amyloid, streptolysin O, and growth hormone.

Kits

The present invention is also directed to a kit to treat LVNC or DC. The kit is an assemblage of materials or components, including at least one MCR antagonist or a pharmaceutical composition comprising same. The exact nature of the components configured in the inventive kit depends on its intended purpose. For example, some embodiments are configured for the purpose of treating LVNC or DC. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use can be included in the kit. "Instructions for use" typically include a tangible expression describing the technique to be employed in using the components of the kit to effect a desired outcome, such as to treat LVNC or DC. Optionally, the kit can also contain other useful components, such as, diluents, buffers, pharmaceutically acceptable carriers, syringes, catheters, applicators, pipetting or measuring tools, or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a glass vial used to contain suitable quantities of an inventive composition. The packaging material generally has an external label which indicates the contents and/or purpose of the kit and/or its components.

Peptides

Various embodiments of the present invention relates to an isolated peptide comprising the amino acid sequence of:

(MCL0020, SEQ ID NO: 1)
Ac-D-2-Nal-Arg-2-Nal-NH$_2$, (SEQ ID NO: 2)
Ac-Nle-cyclo(-Asp-His-D-2-Nal-Arg-Trp-Lys)-NH$_2$, (SEQ ID NO: 3)
Ac-Cys-Glu-His-D-2-Nal-Arg-Trp-Gly-Cys-Prol-Pro-Lys-Asp-NH$_2$, (SEQ ID NO: 4)
Ac-Cys-Nle-Arg-His-D-Nal-Arg-Trp-Gly-Cys-NH$_2$, (SEQ ID NO: 5)
Mpr-Glu-His-D-2-Nal-Arg-Trp-Gly-Cys-Pro-Pro-Lys-Asp-NH$_2$, or combinations thereof.

In some embodiments, the peptide comprises at least one D-amino acid. In some embodiments, the peptide comprises at least one beta-amino acid. In some embodiments, the peptide comprises at least one synthetic amino acid.

In some embodiments, the peptide comprises at least one peptide bond replacement. In some embodiments, the peptide comprises at least one peptide bond replacement selected from the non-limiting group consisting of: urea, thiourea, carbamate, sulfonyl urea, trifluoroethylamine, ortho-(aminoalkyl)-phenylacetic acid, para-(aminoalkyl)- phenylacetic acid, meta-(aminoalkyl)-phenylacetic acid, thioamide, tetrazole, boronic ester, olefinic group, and derivatives thereof.

In some embodiments, the peptide comprises at least one amino acid selected from the non-limiting group consisting of: amino acid analogs, chemically modified amino acids, non-natural amino acids, homocysteine, phosphoserine, phosphothreonine, phosphotyrosine, hydroxyproline, hydroxylysine, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In one aspect, the technology described herein relates to an isolated nucleic acid encoding any of the peptides described herein. In one aspect, the technology described herein relates to an expression vector comprising an isolated nucleic acid encoding any of the peptides described herein. Alterations of the original amino acid sequence can be accomplished by any of a number of known techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. In some embodiments, an isolated peptide as described herein can be chemically synthesized and mutations can be incorporated as part of the chemical synthesis process.

Variants can comprise conservatively substituted sequences, meaning that one or more amino acid residues of an original peptide are replaced by different residues, and that the conservatively substituted peptide retains a desired activity, i.e., the ability antagonize a MCR or a MCR pathway. Examples of conservative substitutions include substitution of amino acids that do not alter the secondary and/or tertiary structure of SEQ ID NOs: 1-5 and/or substitutions that do not change the overall or local hydrophobic/ hydrophilic character, substitutions that do not change the overall or local charge, substitutions by residues of equivalent sidechain size, or substitutions by sidechains with similar reactive groups. Other examples involve substitution of amino acids that have not been evolutionarily conserved in the parent sequence across species.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics or substitutions of residues with similar sidechain volume are well known. Peptides comprising conservative amino acid substitutions can be tested in any one of the assays described herein to confirm that a desired activity, e.g. MCR antagonistic activity, is retained, as determined by the assays described elsewhere herein.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile, Phe, Trp; (2) neutral hydrophilic: Cys, Ser, Thr, Asn, Gln, Ala, Tyr, His, Pro, Gly; (3) acidic: Asp, Glu; (4) basic: His, Lys, Arg; (5) residues that influence chain orientation: Gly, Pro; (6) aromatic: Trp, Tyr, Phe, Pro, His, or hydroxyproline. Non-conservative substitutions will entail exchanging a member of one of these classes for another class. Particularly preferred conservative substitutions for use in the variants described herein are as follows: Ala into Gly or into Ser; Arg into Lys; Asn into Gln or into His; Asp into Glu or into Asn; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr or into Phe; Tyr into Phe or into Trp; and/or Phe into Val, into Tyr, into Ile or into Leu. In general, conservative substitutions encompass residue exchanges with those of similar physicochemical properties (i.e. substitution of a hydrophobic residue for another hydrophobic amino acid).

Any cysteine residue not involved in maintaining the proper conformation of the isolated peptide as described herein can also be substituted, generally with serine, to improve the oxidative stability of the molecule and prevent aberrant crosslinking. Conversely, cysteine bond(s) can be added to the isolated peptide as described herein to improve its stability or facilitate multimerization.

In some embodiments, an isolated peptide as described herein can comprise a mutation that locks the peptide into a beta strand conformation or otherwise constrained conformation. In some embodiments, the mutation is a double Cys mutation. In some embodiments the mutation allows assembly of beta strands via click chemistry, e.g. fragments or subsections of a peptide can be expressed and/or synthesized together or separately and joined together by any suitable click chemistry method to form beta strands or click chemistry moieties at at least two locations in the peptide can lock the peptide in a beta strand conformation or otherwise constrained conformationally. Mutations that lock or constrain the peptide can be located at any point along the amino acid sequence of the peptide, e.g. at both ends of the peptide or at any position not at the ends of the peptide. Click chemistry methods and compositions are well known to one of ordinary skill in the art and are described in, for example, U.S. Pat. No. 7,375,234 and U.S. Patent Publications 2005/0032081; 2011/0224383; 2010/0136034; and 2010/0081137; and Dieterich et al. PNAS 2006 103:9482-7; Best, M. D. Biochemistry 2009 48:6571-6584; Gunasekaran et al. Protein Engineering 1997 10:1131-1141; and Rajagopal et al. European Biophysics Journal 2006 35:162-9; each of which is incorporated by reference herein in its entirety.

In some embodiments, an isolated peptide as described herein can comprise at least one peptide bond replacement. A single peptide bond or multiple peptide bonds, e.g. 2 bonds, 3 bonds, 4 bonds, 5 bonds, or 6 or more bonds, or all the peptide bonds can be replaced. An isolated peptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof.

In some embodiments, an isolated peptide as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In some embodiments, an isolated peptide as described herein can comprise alternative amino acids, amino acid analogs, chemically modified amino acids, or non-natural amino acids. Non-limiting examples of alternative amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In some embodiments, an isolated peptide can be modified, e.g. a moiety can be added to one or more of the amino acids comprising the peptide. In some embodiments, an isolated peptide as described herein can comprise one or more moiety molecules, e.g. 1 or more moiety molecules per peptide, 2 or more moiety molecules per peptide, 5 or more moiety molecules per peptide, 10 or more moiety molecules per peptide or more moiety molecules per peptide. In some embodiments, an isolated peptide as described herein can comprise one or more types of modifications and/or moieties, e.g. 1 type of modification, 2 types of modifications, 3 types of modifications or more types of modifications. Non-limiting examples of modifications and/or moieties include PEGylation; post-traslational derivitzations; glycosylation; hydroxylation; methylation; HESylation; ELPylation; lipidation; acetylation; amidation; biotinylation; end-capping modifications; cyano groups; phosphorylation; cyclization; or other conjugation moieties (e.g. protein, antibody, peptide, nucleotide, virus, phage, matrix, insoluble support, particle, etc.). In some embodiments, an end-capping modification can comprise acetylation at the N-terminus, N-terminal acylation, and N-terminal formylation. In some embodiments, an end-capping modification can comprise amidation at the C-terminus, introduction of C-terminal alcohol, aldehyde, ester, and thioester moieties.

Exemplary embodiments of the various aspects disclosed herein can be described by one or more of the following numbered paragraphs:

1. A method for treating left ventricular non-compaction cardiomyopathy (LVNC) or dilated cardiomyopathy (DC) comprising:
   administering a therapeutically effective amount of a melanocortin receptor four (MC4R) antagonist to a subject in need thereof.
2. The method of paragraph 1, wherein the MCR antagonist is selected from the group consisting of peptides, peptide analogs and derivatives, peptidomimetics, proteins, small organic or inorganic molecules, antibodies, antigen or epitope binding fragments of antibodies, nucleic acids, nucleic acid analogs and derivatives, an extract made from biological materials, and any combinations thereof
3. The method of paragraph 1 or 2, wherein the MC4R antagonist is selected from the group consisting of:

(MCL0020, SEQ ID NO: 1)
   Ac-D-2-Nal-Arg-2-Nal-NH$_2$;

(SHU9119, SEQ ID NO: 2)
   Ac-Nle-cyclo(Asp-His-D-2-Nal-Arg-Trp-Lys)-NH$_2$;

(HS014, SEQ ID NO: 3)
   Ac-Cys-Glu-His-D-2-Nal-Arg-Trp-Gly-Cys-Prol-Pro-Lys-Asp-NH$_2$;

(HS024, SEQ ID NO: 4)
   Ac-Cys-Nle-Arg-His-D-Nal-Arg-Trp-Gly-Cys-NH$_2$;

(JKC363, SEQ ID NO: 5)
   Mpr-Glu-His-D-2-Nal-Arg-Trp-Gly-Cys-Pro-Pro-Lys-Asp-NH$_2$;

Ac-Cys-Glu-His-(diCl-D-Phe)-Arg-Trp-Gly-Cys-Pro-Pro-Lys-Asp-NH$_2$, wherein diCl-D-Phe is a dichloro-D-phenylalanine (HS028, SEQ ID NO: 6); Compound 10, Pontillo14c, Compound 10d, Compound 18v, Compound 13b-2, Compound Tran12e, and Compounds Xi14a-j, as described in US20100129319; HS131; BL-6020/979; MCL0129; MPB-10; MCL-0042; Agouti-related peptides; and any combinations thereof.
4. The method of any of paragraphs 1-3, wherein the MCR antagonist is selected from the group consisting of MCL0020, SHU9119, HS014, HS024, JKC36, and any combinations thereof.
5. The method of any of paragraphs 1-4, further comprising selecting the subject for treatment.
6. The method of paragraph 5, wherein said selecting comprises diagnosing the subject for LVNC or DC.

7. The method of paragraph 5 or 6, wherein said selecting comprises assaying a biological sample from the subject.
8. The method of any of paragraphs 1-6, wherein the subject has a mutation in the PR domain containing 16 (PRDM 16) gene.
9. The method of paragraph 8, wherein said mutation in PRDM 16 gene is selected from the group consisting of truncation, frameshift and missense mutations.
10. The method of paragraph 8 or 9, wherein said mutation are c.811G>A (p.Glu271Lys), c.872C>T (p.Pro291Leu), c.1573dupC (p.Arg525Profs*79), c.2104A>T (p.Lys702*), c.2447A>G (p.Asn816Ser), c.2660T>C (p.Leu887Pro), c.3301G>A (p.Val2202Met).
11. The method of any of paragraphs 1-10, further comprising co-administering a LVNC or DC management therapy to the subject.
12. The method of paragraph 11, wherein said management therapy is selected from the group consisting of pacemaker, biventricular pacing devices, left ventricular assist device, implantable cardioverter-defibrillator (ICD), heart bypass (CABG) surgery, angioplasty, valve replacement or repair, heart transplant, artificial heart implant, and any combinations thereof
13. The method of any of paragraphs 1-12, wherein the subject is currently being treated for LVNC or DC.
14. The method of any of paragraphs 1-13, wherein the MCR antagonist is formulated in a pharmaceutical composition comprising a pharmaceutically acceptable excipient or carrier.

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

Some Selected Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular. Thus, as used herein and in the claims, the singular forms include the plural reference and vice versa unless the context clearly indicates otherwise. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

As used herein the term "comprising" or "comprises" is used in reference to compositions, methods, and respective component(s) thereof, that are useful to an embodiment, yet open to the inclusion of unspecified elements, whether useful or not. The term "comprising" or "comprises" include "consisting essentially of" and "consisting of."

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages can mean 5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviations (2SD) away from a reference level. The term refers to statistical evidence that there is a difference. It is defined as the probability of making a decision to reject the null hypothesis when the null hypothesis is actually true.

As used interchangeably herein, the terms "essentially" and "substantially" means a proportion of at least about 60%, or preferably at least about 70% or at least about 80%, or at least about 90%, at least about 95%, at least about 97% or at least about 99% or more, or any integer between 70% and 100%. In some embodiments, the term "essentially" means a proportion of at least about 90%, at least about 95%, at least about 98%, at least about 99% or more, or any integer between 90% and 100%. In some embodiments, the term "essentially" can include 100%.

As used herein, the terms "treat," "treatment," "treating," or "amelioration" are used herein to characterize a method or process that is aimed at (1) delaying or preventing the onset of a disease or condition; (2) slowing down or stopping the progression, aggravation, or deterioration of the symptoms of the disease or condition; (3) bringing about ameliorations of the symptoms of the disease or condition; or (4) curing the disease or condition. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased morbidity or mortality. The term "treatment" of a disease also includes providing relief from the symptoms or side-effects of the disease (including palliative treatment). A treatment can be administered prior to the onset of the disease, for a prophylactic or preventive action. Alternatively or additionally, the treatment can be administered after initiation of the disease or condition, for a therapeutic action. It is to be understood that "treatment" and "treating," as used herein refer to both therapeutic treatment and prophylactic or preventative measures, wherein the object is to prevent, slow down and/or alleviate the disease or disease condition even if the treatment is ultimately unsuccessful.

As used herein, "beneficial results" can include, but are in no way limited to, lessening or alleviating the severity of the disease condition, preventing the disease condition from worsening, curing the disease condition and prolonging a patient's life or life expectancy.

As used herein, the term "small molecule" can refer to compounds that are "natural product-like." However, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons. In some embodiments, "small molecule" as used herein refers to an organic compound that may serve a regulator or a biological process of the present invention and whose molecular weight limit is approximately 900 Dalton, allowing for the possibility to rapidly diffuse across cell membranes so that they can reach intracellular sites of action.

As used herein, the term "therapeutic agent" refers to any substance used internally or externally as a medicine for the treatment, cure, prevention, slowing down, or lessening of a disease or disorder, even if the treatment, cure, prevention, slowing down, or lessening of the disease or disorder is ultimately unsuccessful.

The term "derivative" as used herein refers to a chemical substance related structurally to another, i.e., an "original" substance, which can be referred to as a "parent" compound. A "derivative" can be made from the structurally-related parent compound in one or more steps. In some embodiments, the general physical and chemical properties of a derivative can be similar to or different from the parent compound.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1

Material and Methods
Study Participants and Clinical Evaluation

Probands with non-syndromic cardiomyopathy were recruited at tertiary referral centers, the Charité University Hospital and the German Heart Institute, both in Berlin, Germany, the University Hospital Zurich, Switzerland, and the Harefield Hospital, Harefield, United Kingdom. Informed consent was obtained from all participants according to institutional guidelines. Probands and available family members were evaluated by echocardiography and clinical examination. LVNC and DCM were diagnosed on the basis of established criteria. LVNC patients the majority already screened for known mutations in sarcomere genes, were enrolled in the study. For RNA-Seq studies, explanted heart biopsies samples from patients with confirmed DCM were used with local ethical approval.
Mutational Analysis PCR and Sanger sequencing of PRDM16 in probands with LVNC and DCM were performed with standard methods. Primer sequences and PCR details are available on request. Sequences were analyzed with Sequencher 4.10.1 (Gene Codes Corporation).

In the 131 DCM patients polyA RNA was sequenced on the Illumina HiSeq 2000 platform using TruSeq library preparation and 2×100 bp paired-end sequencing chemistry. Reads were mapped stringently against the hg19 reference genome with Tophat 1.3.1, allowing only a total of 2 mismatches in 100 bp and supplying transcript information as annotated by the Ensembl database to aid the mapping process. SNP calling in the coding region of PRDM16 was performed with SAMtools only with reads mapping uniquely to the genome. Genomic positions covered with more than 15 unique reads (no PCR duplicates) were considered for SNP detection. The 5 identified variants were not identified in 362 local control chromosome, and were not listed by the 1000 Genomes Project or detected in the more than 6400 control individuals of the Exome Sequencing Project (ESP) and were thus considered novel. Considering the prevalence of missense variants in the gene PRDM16 (n=55 in 6400 exomes) in the ESP control population we would expect only ~1.2 novel mutations in a set of 131 individuals. The significant enrichment of novel non-synonymous variants affecting PRDM16 in the cohort further supports a role for PRDM16 in DCM. All novel mutations were confirmed by Sanger Sequencing.

Morpholine Antisense Oligonucleotide Injections

Morpholinos directed against the translation start codon were 5'-TCATCGCTGTCTTCCCGCTCCTGCT (SEQ ID NO: 7) for prdm16 (Gene Tools (Philomath, Oreg.)) and were injected at the one cell stage. Concentrations of 0.2 mM were used.

Cardiac Overexpression

For cardiac-specific overexpression experiments the human PRDM16 truncation mutation (p.K702X) and the human PRDM16 wildtype were cloned downstream of the cmlc2 promoter into the Tol2kit expression system using Gateway technology (Invitrogen). PRDM16 constructs (15 ng/µl) were co-injected with 10 ng/µl capped Tol2 transposase mRNA into one-cell-stage zebrafish embryos.

For the ARVC model a UAS/2057del2 plakoglobin (UAS: Naxos) responder construct was created using the Gateway cloning system (Invitrogen). Single-cell embryos were injected with destination vector DNA (15 ng/nl) and Tol2 transposase RNA (15 ng/nl).

Rescue Experiments

MC4 receptor antagonists and agonists were dissolved in 100% DMSO to a stock concentration of 1 mM. Working solutions were diluted in nuclease free water. The concentrations for MCL0020, HS014, SU9119 were 1 µM, for JKC363 2 µM, HS024 200 nM and for the MC4 receptor agonist THIQ 1 µM and 500 µM. 1 nl of the dilution of MC4 receptor antagonists was injected into the yolk sac of a zebrafish embryo at the one-cell stage for studies with PRDM16.

Homozyous UAS:Naxos fish were crossed with cmlc2: nppb:luciferase fish. and were injected at 24 hpf (hours post fertilization) with either 1 µM MCL0020, HS014, SU9119, 2 µM JKC363 or 200 nM HS024 into the yolk sac. Embryos were therefore anesthetized with 0.015% tricain solution and positioned in an agar mold. At 72 hpf fish were arrayed in a 96-well plate in E3 water and an equal volume of long half-life luciferase reagent (Promega). The plate was incubated for 1 hour in the dark and activities were measured with a Victor 3 luminometer (Perkin Elmer).

Norepinephrine was dissolved in 100% DMSO to a stock concentration of 1 mM. Working solutions of 10 nM, 100 nM or 1 µM were diluted in 20 ml E3 water and zebrafish embryos were incubated directly after birth. Cardiac function was assessed at 48 hpf as described below.

Zebrafish Physiologic Analysis

For analysis of cardiac function embryos were laterally positioned and allowed to acclimate at 24° C. Video microscopy was performed on an Axioplan (Zeiss) upright microscope with a FastCam-PCI high-Speed digital camera (Photron) on top. 1088 frames were digitally captured at identical frame rates (250 frames per second) and magnification (5×). Sequential images were analyzed for heart rate and cardiac output using IMAGEJ and Excel. Experiments were repeated at least 3 times on each occasion using 10 animals. Intercellular coupling parameters in zebrafish embryo hearts were measured using previously reported techniques. Briefly, hearts were isolated from zebrafish embryos, stained with the transmembrane-potential-sensitive dye di-8-ANEPPS (Invitrogen) and placed into a perfusion chamber that was mounted onto the stage of an inverted microscope. Excitation light from a high-intensity Hg arc lamp was transmitted through a 525/50-nm bandpass filter and reflected onto the preparation via a 565-nm dichroic mirror. Fluorescence emission was filtered by a 685/80-nm bandpass filter and recorded at a rate of 2000 $s^{-1}$ by a high-speed CCD camera (CardioCCD-SMQ, RedshirtImaging, LLC). Single-pixel action potentials were extracted from the fluorescence data and conduction velocities were estimated using an established algorithm. Experiments were repeated at least 2 times with 5 animals.

Immunofluorescence, Detection of Apotosis and Mitochondrial Assessment

For proliferation detection hearts from 48 hpf old zebrafish embryos were isolated and fixed in Prefer fixative (Anatech). The fixed hearts were stained with the primary antibodies rabbit anti-PCNA 1:200 (Abcam) and mouse anti-MF20 1:100 (DSHB), and the secondary antibodies donkey or goat anti-rabbit or mouse Alexa 488 or 546 conjugated (Invitrogen) 1:1,000. Hearts were mounted with ProLong Antifade reagent with DAPI mounting medium on a slide. Confocal images were analyzed using IMAGEJ.

For detection of apoptosis hearts from 48 hpf old zebrafish embryos were isolated and fixed in 4% PFA/PBS for 30 min and washed twice in PBS-T for 30 min. TUNEL assay was performed by using the in situ cell detection kit from Roche. Hearts were mounted with ProLong Antifade reagent with DAPI on a slide and confocal images were analyzed using IMAGEJ.

For mitochondrial membrane potential assessment hearts from 48 hpf old zebrafish embryos were isolated and stained with DeepRedFM (Invitrogen) 1:300 (1 mM stock) and RedCMXRos (Invitrogen) 1:300 (1 mM stock) for 1 hour. Hearts were washed 3 times in PBS-T for 15 min and then fixed in 4% PFA/PBS for 15 min, then washed once in PBS-T. Hearts were mounted with ProLong Antifade reagent with DAPI on a slide and confocal images were analyzed using IMAGEJ.

For oxidative stress detection hearts from 48 hpf old zebrafish embryos were isolated and stained with 50 µM CellROX (Invitrogen) in PBS-T for 30 min. Hearts were washed twice in PBS-T for 10 min and then fixed in 4% PFA/PBS for 5 min, then washed once in PBS-T. Hearts were mounted with ProLong Antifade reagent with DAPI on a slide and confocal images were analyzed using IMAGEJ.

Echocardiography 3 month old cmlc2:PRDM16 mutant zebrafish and wildtype siblings were positioned with belly up in a fish water soaked sponge. Aortic peak velocity was measured by 45 MHz pulse-wave Doppler with a Visualsonics Vevo2100 echo machine.

Transmission Electron Microscopy (TEM)

Isolated hearts of age-matched adult zebrafish were fixed in 5% glutaraldehyde, 2.5% paraformaldehyde, 0.06% picric acid in 0.2M Cacodylate buffer for 1 day and then resin embedded using a standard fixation protocol for TEM. Hearts were sectioned ultrathin and images were at 3.000×, 8.000×, 12.000× and 20.000× of magnification. Images were analyzed using IMAGEJ.

Statistical Analysis

For functional experiments in zebrafish one-Way ANOVA was used. Data are presented as means±s.e.m. $P<0.05$ was considered statistically significant for all tests; *=$P<0.05$.

MC4 receptor antagonists can rescue cardiomyopathy in different zebrafish disease models. Recently identified mutations in the PRDM 16 gene as a cause of syndromic and non-syndromic left ventricular non-compaction and cardiomyopathy. High-throughput screening is used explore the biology and potential therapies for this novel disease pathway in newly generated zebrafish. To examine the effect of PRDM16 mutations knockdown of the zebrafish ortholog of PRDM16 using translation-blocking morpholinos to recapitulate potential haploinsufficiency were performed. Fish transgenic were also generated for the truncated mutant form of PRDM16 (p.K702X) driven by the cardiac-specific cmlc2 promoter. Cardiac output was significantly reduced in both morphant and in truncation mutant transgenics when compared with controls (p<0.0005). The contractile impairment in both the morphant knockdown embryos and in the truncation mutant transgenics was efficiently rescued by all 5 available peptide MC4 receptor antagonists, which were injected at the one-cell stage (MCL0020, SU9119, JKC363, HS014 and HS024), in a dose-dependent manner. Semiautomated cell counting documented a significant decrease in total cardiomyocyte numbers in PRDM16 morphant hearts when compared to WT controls at 48 hours post fertilization (hpf). This was associated with significantly decreased cardiomyocyte proliferation (percentage of PCNA positive cells) in the hearts of the morphant and the truncation mutant hearts at 48 hpf. In addition, there was evidence of a concomitant increase in apoptosis in the PRDM16 mutants at 48 hpf using either TUNEL assay p or annexin V transgenic reporter lines. Both observations were completely restored by the application of the MC4R antagonists. It also seems that the antagonist alone might have a pro-proliferative effect. Proliferation is often reciprocally related to cell coupling. In murine models where LVNC is observed, it has been associated with evidence of partial cellular uncoupling, so the effects of PRDM16 on intercellular impulse propagation across the myocardium were tested, identifying a significant reduction in coupling in morphant and in mutant hearts. Mean estimated conduction velocities from the outer curvature of the ventricle (OC) confirm a significant reduction in impulse propagation velocities in morphant and mutant hearts when compared with uninjected controls. This reduction in coupling can be completely prevented by MCL0020. In a next step the novel MC4R antagonists were tested on a different cardiomyopathy model. Naxos zebrafish model were used, which mimics arrhythmogenic right ventricular cardiomyopathy crossed with a nppb-luciferase line, a heart failure marker in the zebrafish. An increase of luciferase activity describes a low cardiac output with heart failure. The Naxos-nppb-luc model develops heart failure with an increase of luciferase activity at 72 hpf. Injection of the peptide MC4R antagonists at 24 hpf into the yolk sac of the embryo can rescue this form of heart failure as shown by the normalization of luciferase activity. Importantly, this intervention did not rescue two other forms of cardiomyopathy that are thought to be mediated by other mechanisms. Together these data suggest that in specific forms of cardiomyopathy resulting from abnormalities of the differentiation of cardiomyocytes manipulation of the MC4R can prevent the emergence of heart failure.

Figure 8A:
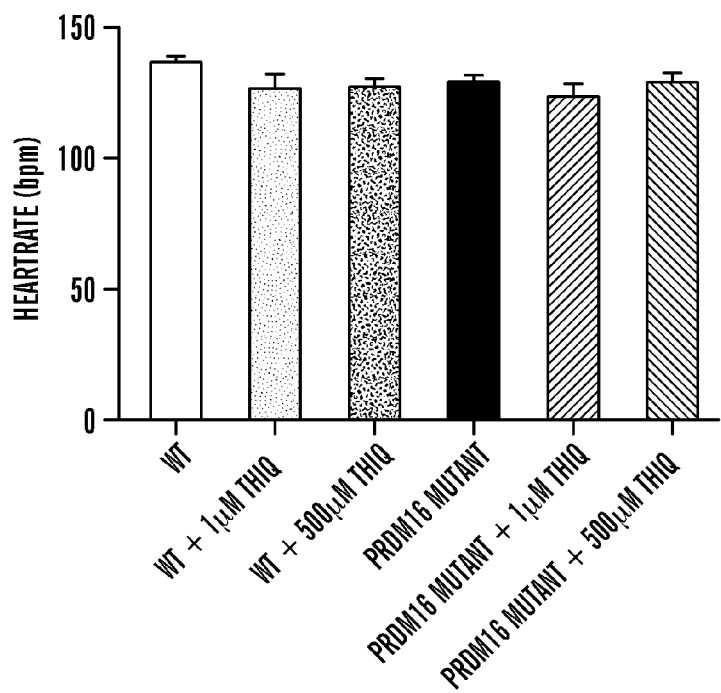
FIGS. 8A and 8B are bar graphs showing MC4R-agonist THIQ is not able to rescue the contractile dysfunction seen in the zebrafish model for cardiomyopathy with PRDM16 truncation. As can be seen, THIQ decreases cardiac output in healthy wildtype zebrafish embryos. The heart rate is not altered. This demonstrates the specificity of the MC4R-antagonist rescue treatment.
Figure 8B:
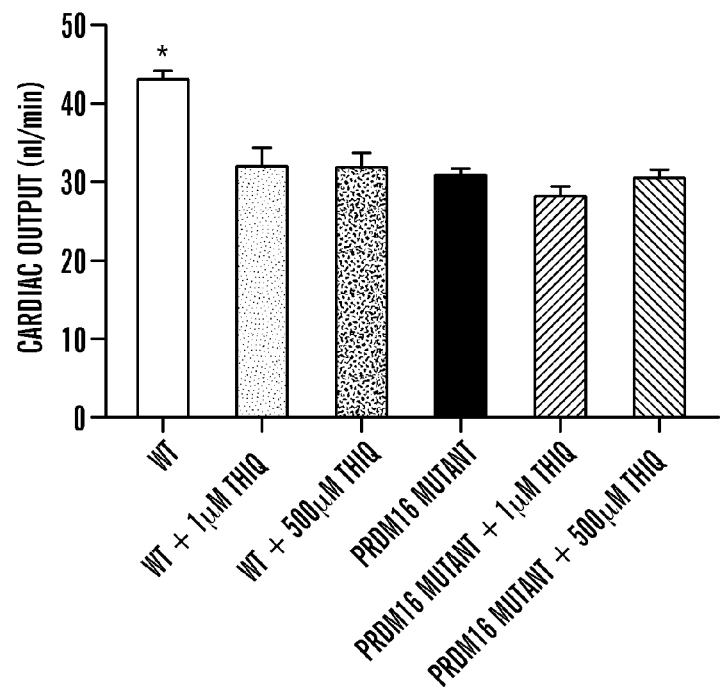

As show in FIGS. 8A and 8B, the MC4R-agonist THIQ is not able to rescue the contractile dysfunction seen in our zebrafish model for cardiomyopathy with PRDM16 truncation. It decreases cardiac output in healthy wildtype zebrafish embryos. The heart rate is not altered. This demonstrates the specificity of MC4R-antagonist rescue treatment.

Figure 9A:
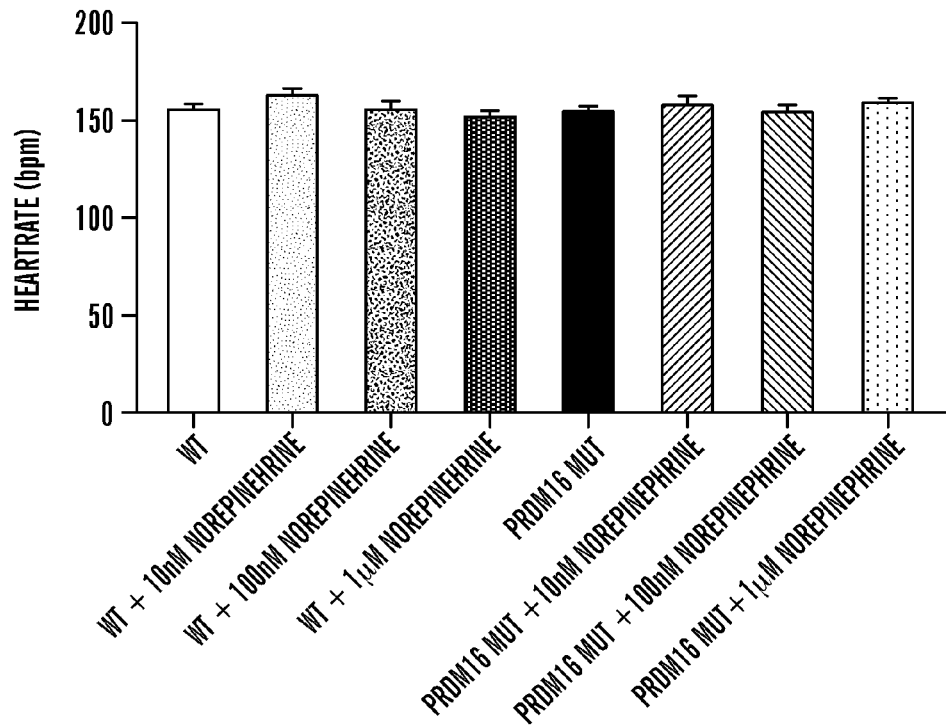
FIGS. 9A and 9B are bar graphs showing treatment of PRDM16 truncation zebrafish model with different doses of norepinephrine since humoral adrenergic signaling and the melanocortin system directly linked. High doses caused necrosis of the tail in PRDM16 mutant model as well as in wildtype fish. Doses of 10 nM up to 1 µM of norepinephrine were able to rescue the contractile dysfunction in the PRDM16 mutant model whereas doses of 100 nM and 1 µM caused decreased cardiac output in wildtype fish.
Figure 9B:
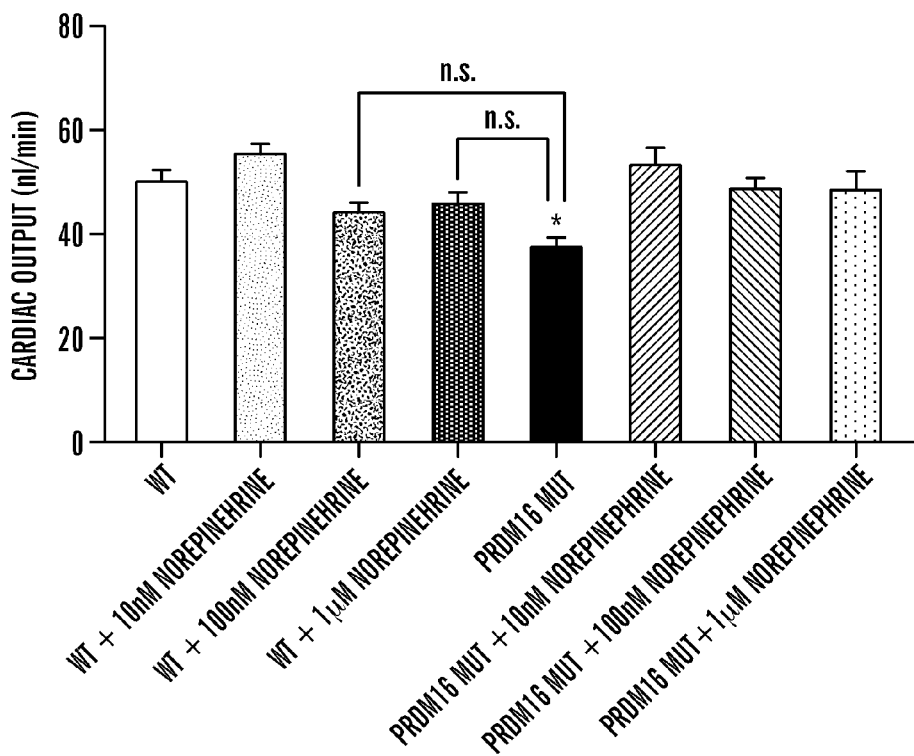

The adrenergic and the melanocortin system are linked with each other especially in terms of obesity and hypertension. For this reason the inventors treated the PRDM16 truncation zebrafish model with different doses of norepinephrine. As seen in FIGS. 9A and 9B, too high doses caused necrosis of the tail in PRDM16 mutant model as well as in wildtype fish. Doses of 10 nM up to 1 µM of norepinephrine were able to rescue the contractile dysfunction in the PRDM16 mutant model whereas doses of 100 nM and 1 µM caused decreased cardiac output in wildtype fish.

Figure 10A:
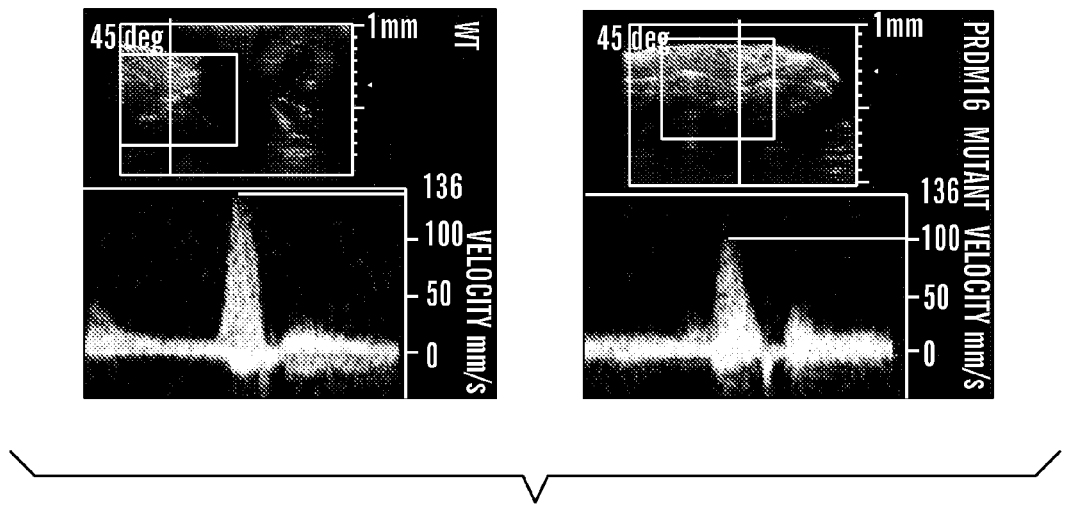
FIGS. 10A and 10B show the phenotype is consistent during the whole life of the fish.
Figure 10B:
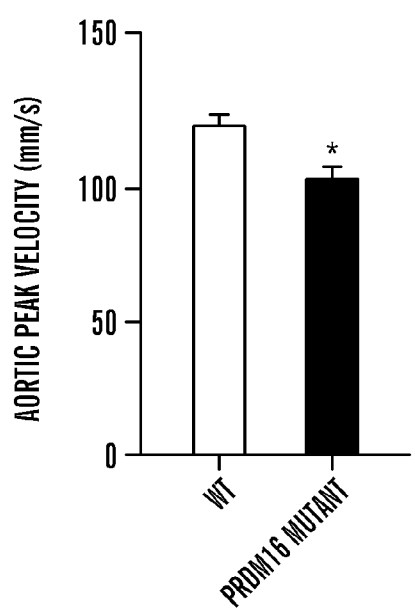

The inventors further studied to see if the phenotype is consistent during the whole life of the fish. The inventors performed echocardiography on the adult PRDM16 mutant zebrafish and their wildtype age-matched siblings (FIG. 10A). A decreased aortic peak velocity was seen in PRDM16 model compared to their wildtype siblings (FIG. 10B). This indicates a decreased cardiac function and validates the PRDM 16 mutant model as a useful model organism to investigate cardiomyopathy.

Figure 11A:
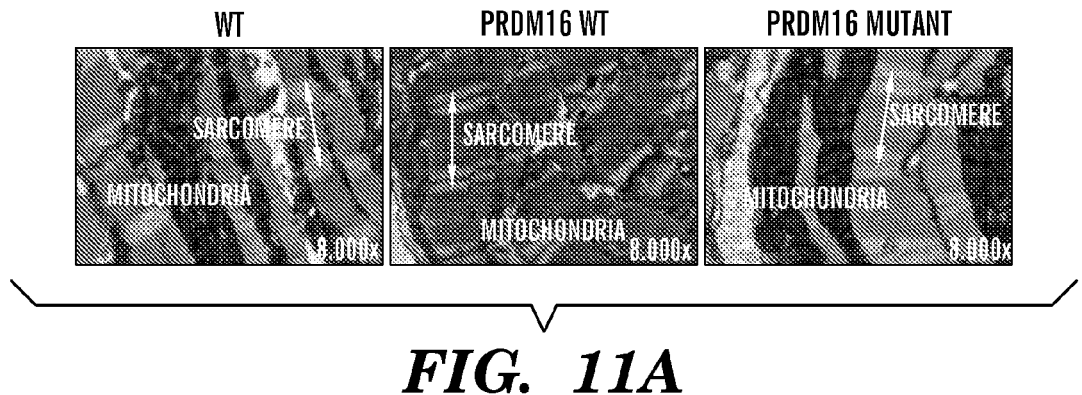
FIG. 11A shows transmission electron microscopy images isolated hearts of PRDM16 mutant zebrafish (right panel) and age-matched wildtype zebrafish (left panel) and zebrafish with PRDM16 wildtype overexpression (middle panel)
Figure 11B:
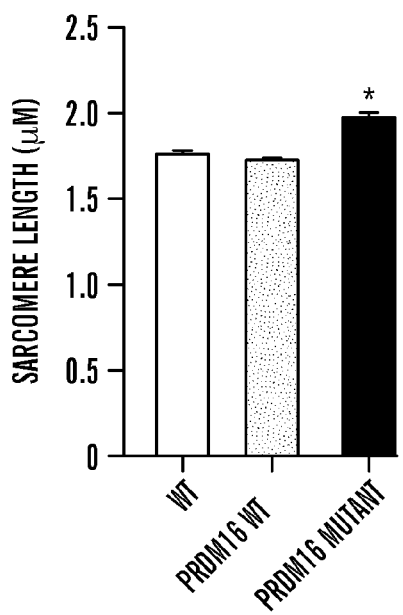
FIGS. 11B and 11C are bar graphs showing increased sarcomere length (FIG. 11) as well as increased number of mitochondria per sarcoma (FIG. 11C) in the PRDM 16 mutant model compared to wildtype and PRDM16 overexpression zebrafish.
Figure 11C:
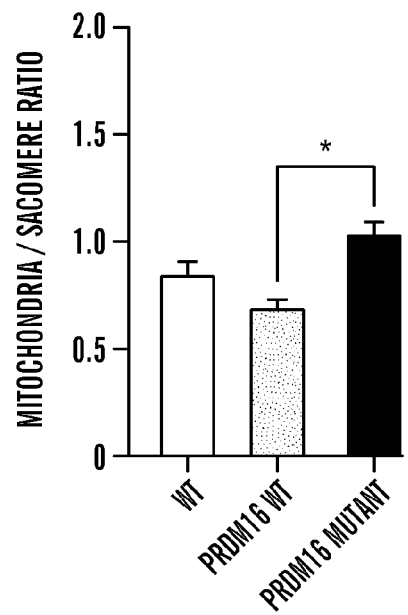

After the validation of the adult zebrafish model, the performed transmission electron microscopy on isolated hearts of these fish. We also included age-matched zebrafish with PRDM16 wildtype overexpression. (FIG. 11A) An increased sarcomere length (FIG. 11C) as well as an increased number of mitochondria per sarcomere (FIG. 11C) was seen in the PRDM16 mutant model compared to wildtype and PRDM16 overexpression zebrafish.

Figure 12A:
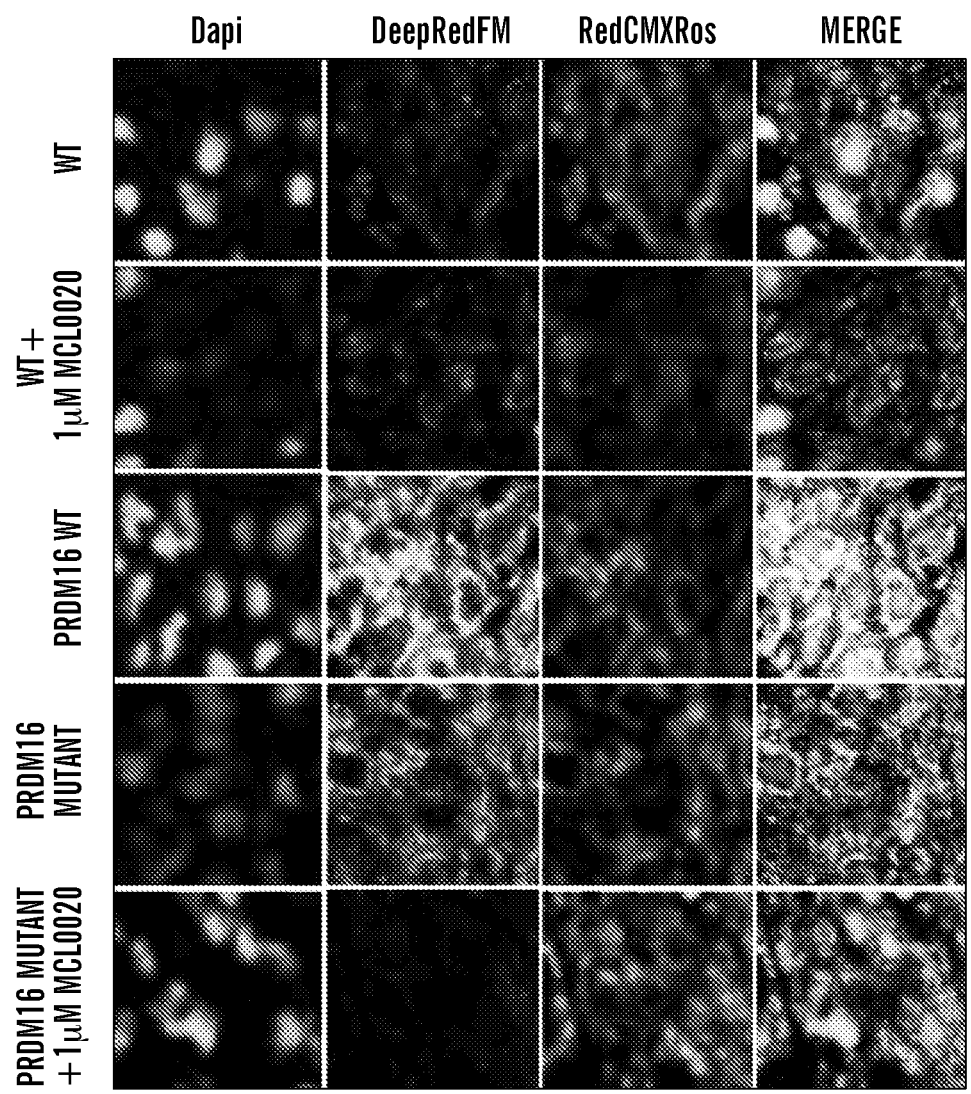
FIG. 12A represents 2 day old isolated zebrafish hearts. Left panel shows nuclear staining with dapi, middle panel shows staining with mitochondrial dye DeepRedFM as a marker for the number of mitochondria and right panel shows staining with the mitochondrial membrane potential dye RedCMXRos.
Figure 12B:
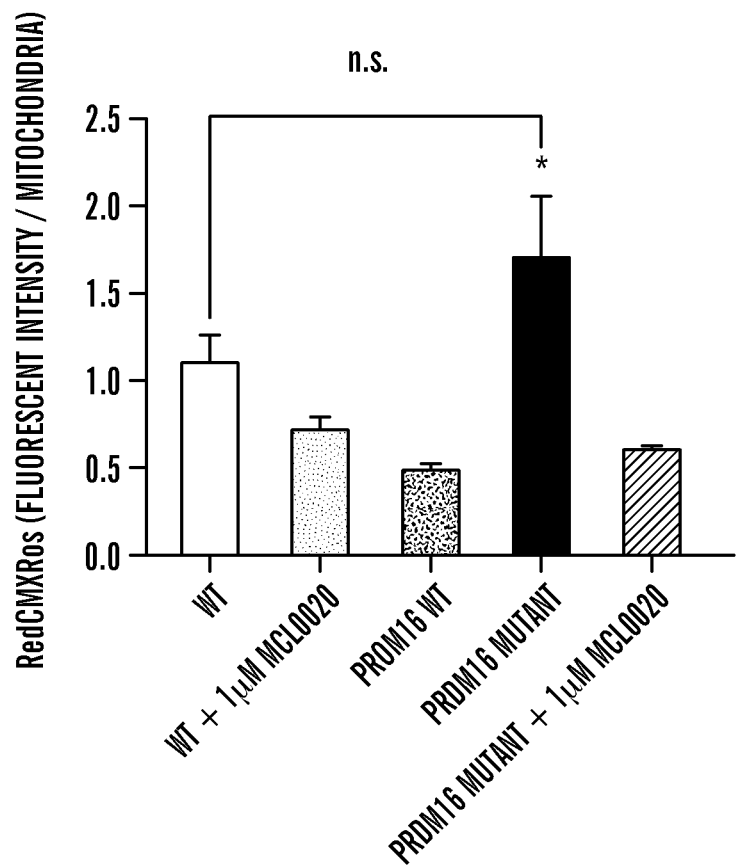
FIG. 12B is a bar graph showing that the PRDM16 mutant hearts showed an increased membrane potential represented as a ratio of the fluorescent intensity of RedCMXRos and DeepRedFM. This alteration can be completely rescued by the treatment with MCL0020.

The inventors then looked at mitochondria in the development model. Isolated hearts of 2-day-old wildtype, PRDM16 overexpression and PRDM16 mutant fish as well as wildtype and PRDM16 mutant fish treated with the MC4R-antagonist MCL0020 were stained with DeepRedFM (grey) as a marker for the number of mitochondria and RedCMXRos (grey), a marker for mitochondrial membrane potential. DAPI (grey) was used to stain the nucleus of the cell (FIG. 12A). The PRDM16 mutant hearts showed an increased membrane potential represented as a ratio of the fluorescent intensity of RedCMXRos and DeepRedFM (FIG. 12B) This alteration was completely rescued by the treatment with MCL0020 (FIG. 12B).

Figure 13A:
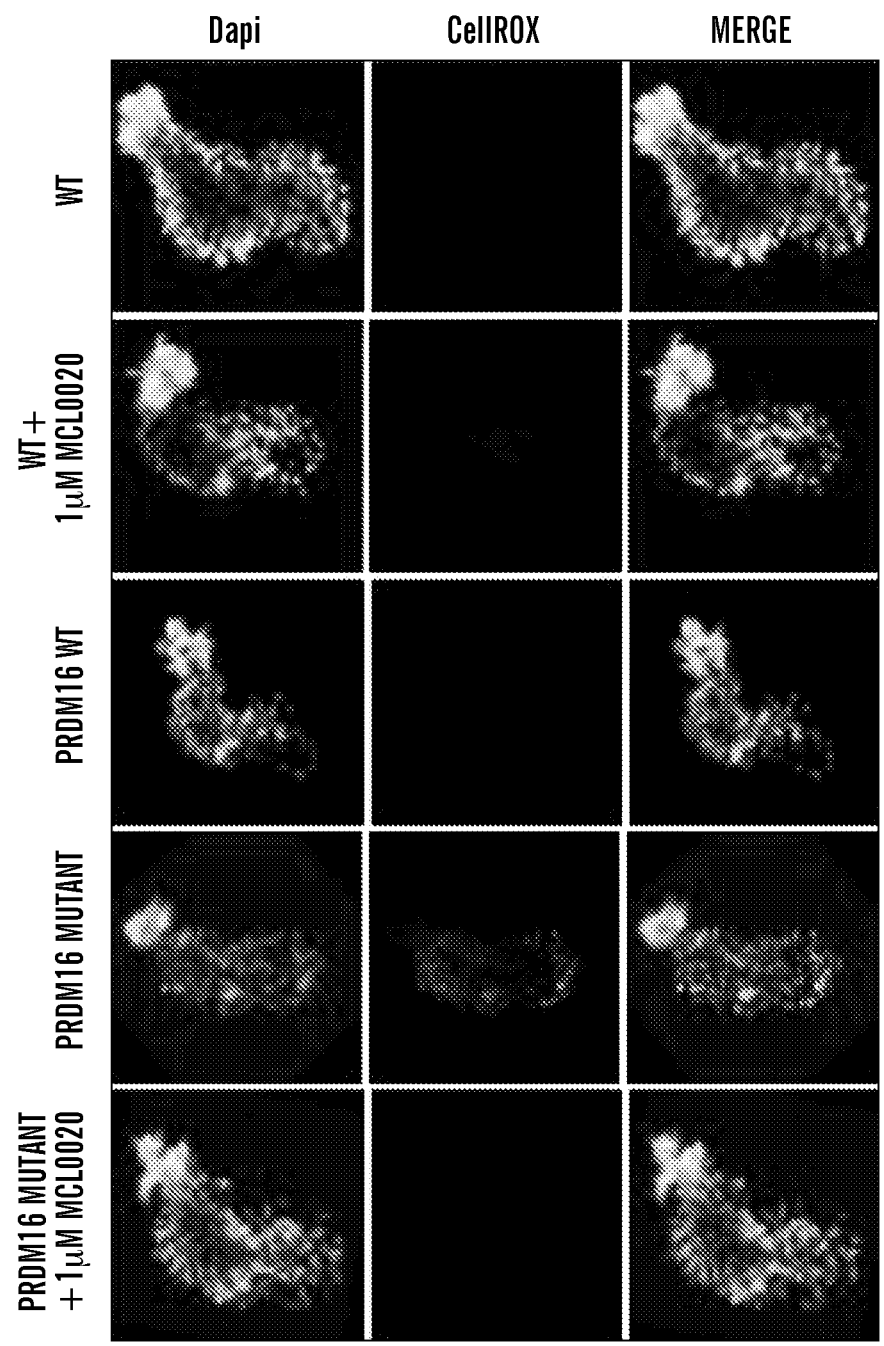
FIG. 13A represents 2 day old isolated zebrafish hearts. Left panel shows nuclear staining with DAPI, right panel shows staining with CellROX, an indicator for oxidative stress.
Figure 13B:
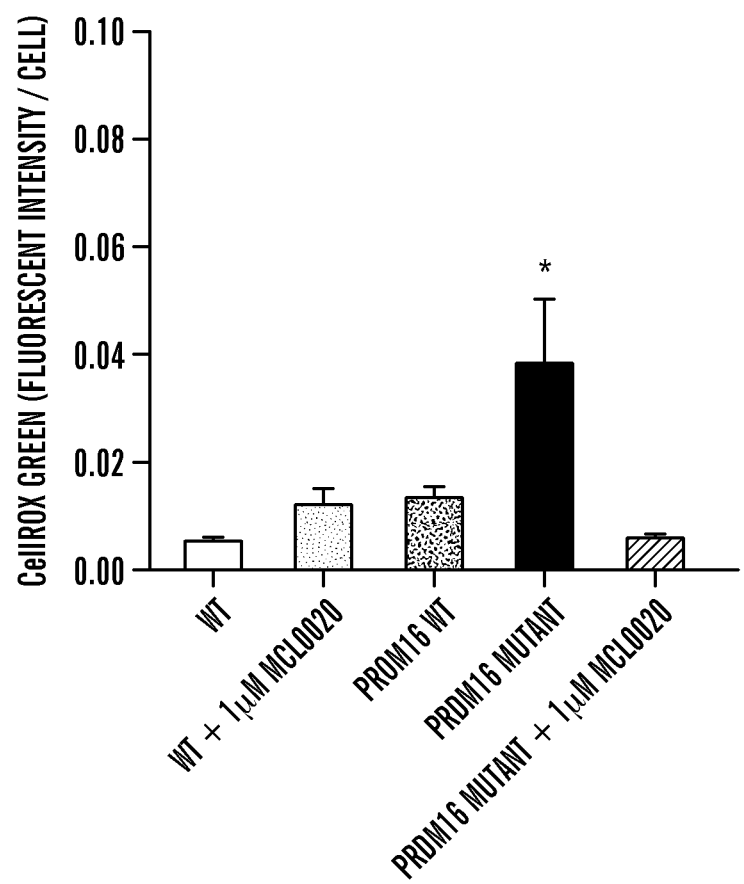
FIG. 13B is a bar graph showing that the PRDM16 mutant hearts showed an increased production of reactive oxygen species. This alteration can be completely rescued by the treatment with MCL0020.

The inventors also looked at oxidative stress which is able to alter mitochondrial membrane potential. We therefore stained 2-day-old isolated hearts from wildtype, PRDM16 overexpression and PRDM16 mutant fish as well as wildtype and PRDM16 mutant fish treated with the MC4R-antagonist MCL0020 with CellROX (grey) which is an indicator for reactive oxygen species (ROS) (FIG. 13A). The hearts of the PRDM16mutant model showed a significant increase in ROS which was completely diminished by MCL0020 (FIG. 13B).

Taken together, the data show that the MC4R antagonist but not the agonist can rescue contractile dysfunction in cardiomyopathy. The contractile impairment can also be rescued by norepinephrine, a member of the adrenergic system and therefore were closely related to the melanocortin system. After the validation of the model in adult stage, the inventors observed an increase in sarcomere length and an increased number of mitochondria. During development the mitochondrial membrane potential is altered accompanied with an increase in production of reactive oxygen species in our model. These observations can all be rescued by antagonism of α-MSH at the MC4-receptor.

While particular embodiments of various aspects disclosed herein have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method for treating left ventricular non-compaction cardiomyopathy (LVNC) or dilated cardiomyopathy (DC) comprising:

administering a therapeutically effective amount of a melanocortin receptor four (MC4R) antagonist to a subject in need thereof, wherein the antagonist is (MCL0020, SEQ ID NO: 1)
Ac-D-2-Nal-Arg-2-Nal-NH$_2$;

(SHU9119, SEQ ID NO: 2)
Ac-Nle-cyclo(Asp-His-D-2-Nal-Arg-Trp-Lys)-NH$_2$;

(HS014, SEQ ID NO: 3)
Ac-Cys-Glu-His-D-2-Nal-Arg-Trp-Gly-Cys-Prol-Pro-Lys-Asp-NH$_2$;

(HS024, SEQ ID NO: 4)
Ac-Cys-Nle-Arg-His-D-Nal-Arg-Trp-Gly-Cys-NH$_2$;

(JKC363, SEQ ID NO: 5)
Mpr-Glu-His-D-2-Nal-Arg-Trp-Gly-Cys-Pro-Pro-Lys-Asp-NH$_2$;

Ac-Cys-Glu-His-(diCl-D-Phe)-Arg-Trp-Gly-Cys-Pro-Pro-Lys-Asp-NH$_2$, wherein diCl-D-Phe is a dichloro-D-phenylalanine (HS028, SEQ ID NO: 6); Compound 10; Pontillo14c; Compound 10d; Compound 18v; Compound 13b-2; Compound Tran12e; Compound Xi14a; Compound Xi14b; Compound Xi14c; Compound Xi14d; Compound Xi14e; Compound Xi14f; Compound Xi14g; Compound Xi14h; Compound Xi14i; Compound Xi14j; HS131; MCL0129; MPB-10; MCL-0042; Agouti 1-40; Agouti 87-132; and any combinations thereof.

2. The method of claim 1, wherein the MC4R antagonist is selected from the group consisting of:

(MCL0020, SEQ ID NO: 1)
Ac-D-2-Nal-Arg-2-Nal-NH$_2$;

(SHU9119, SEQ ID NO: 2)
Ac-Nle-cyclo(Asp-His-D-2-Nal-Arg-Trp-Lys)-NH$_2$;

(HS014, SEQ ID NO: 3)
Ac-Cys-Glu-His-D-2-Nal-Arg-Trp-Gly-Cys-Pro-Pro-Lys-Asp-NH$_2$;

(HS024, SEQ ID NO: 4)
Ac-Cys-Nle-Arg-His-D-Nal-Arg-Trp-Gly-Cys-NH$_2$;

(JKC363, SEQ ID NO: 5)
Mpr-Glu-His-D-2-Nal-Arg-Trp-Gly-Cys-Pro-Pro-Lys-Asp-Nh$_2$;

wherein diCl-D-Phe is a dichloro-D-phenylalanine (HS028, SEQ ID NO: 6); Compound 10; Pontillo14c; Compound 10d; Compound 18v; Compound 13b-2; Compound Tran12e; Compound Xi14a; Compound Xi14b; Compound Xi14c; Compound Xi14d; Compound Xi14e; Compound Xi14f; Compound Xi14g; Compound Xi14h; Compound Xi14i; Compound Xi14j; HS131; MCL0129; MPB-10; MCL-0042; and any combinations thereof.

3. The method of claim 1, wherein the MC4R antagonist is selected from the group consisting of MCL0020, SHU9119, HS014, HS024, JKC36, and any combinations thereof.

4. The method of claim 1, further comprising selecting the subject for treatment.

5. The method of claim 4, wherein said selecting comprises diagnosing the subject for LVNC or DC.

6. The method of claim 4, wherein said selecting comprises assaying a biological sample from the subject.

7. The method of claim 1, wherein the subject has a mutation in the PR domain containing 16 (PRDM 16) gene.

8. The method of claim 7, wherein said mutation in PRDM 16 gene is selected from the group consisting of truncation, frameshift and missense mutations.

9. The method of claim 8, wherein said mutation is c.811G>A (p.Glu271Lys), c.872C>T (p.Pro291Leu), c.1573dupC (p.Arg525Profs*79), c.2104A>T (p.Lys702*), c.2447A>G (p.Asn816Ser), c.2660T>C (p.Leu887Pro), or c.3301G>A (p.Val2202Met).

10. The method of claim 1, further comprising co-administering a LVNC or DC management therapy to the subject.

11. The method of claim 10, wherein said management therapy is selected from the group consisting of pacemaker, biventricular pacing devices, left ventricular assist device, implantable cardioverter-defibrillator (ICD), coronary artery bypass graft (CABG) surgery, angioplasty, valve replacement or repair, heart transplant, artificial heart implant, and any combinations thereof.

12. The method of claim 1, wherein the subject is currently being treated for LVNC or DC.

13. The method of claim 6, wherein the MC4R antagonist is formulated in a pharmaceutical composition comprising a pharmaceutically acceptable excipient or carrier.

* * * * *

```
                         SEQUENCE LISTING

<160> NUMBER OF SEQ ID NOS: 7

<210> SEQ ID NO 1
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: D-2-Nal
<220> FEATURE:
<221> NAME/KEY: MOD_RES
<222> LOCATION: (3)..(3)
<223> OTHER INFORMATION: 2-Nal
<220> FEATURE:
<223> OTHER INFORMATION: C-term NH2

<400> SEQUENCE: 1

Xaa Arg Xaa
1

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: misc_feature
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<223> OTHER INFORMATION: C-term NH2

<400> SEQUENCE: 2

Xaa Asp His Xaa Arg Trp Lys
1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(8)
<223> OTHER INFORMATION: Cyclic
<220> FEATURE:
```

```
<221> NAME/KEY: MOD_RES
<222> LOCATION: (4)..(4)
<223> OTHER INFORMATION: D-2-Nal
<220> FEATURE:
<223> OTHER INFORMATION: C-term NH2

<400> SEQUENCE: 3

Cys Glu His Xaa Arg Trp Gly Cys Pro Pro Lys Asp
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(9)
<223> OTHER INFORMATION: Cyclic
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (5)..(5)
<223> OTHER INFORMATION: D-Nal
<220> FEATURE:
<223> OTHER INFORMATION: C-term NH2

<400> SEQUENCE: 4

Cys Xaa Arg His Xaa Arg Trp Gly Cys
1               5

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Mpr
<220> FEATURE:
<221> NAME/KEY: misc_feature
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<223> OTHER INFORMATION: C-term NH2

<400> SEQUENCE: 5

Xaa Glu His Xaa Arg Trp Gly Cys Pro Pro Lys Asp
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
```

```
<220> FEATURE:
<221> NAME/KEY: MOD_RES
<222> LOCATION: (4)..(4)
<223> OTHER INFORMATION: diCl-D-Phe
<220> FEATURE:
<223> OTHER INFORMATION: C-term NH2

<400> SEQUENCE: 6

Cys Glu His Phe Arg Trp Gly Cys Pro Pro Lys Asp
1               5                   10

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tcatcgctgt cttcccgctc ctgct                                              25
```